US007008767B2

(12) United States Patent
Handelsman et al.

(10) Patent No.: US 7,008,767 B2
(45) Date of Patent: Mar. 7, 2006

(54) MICROORGANISM GENOMICS, COMPOSITIONS AND METHODS RELATED THERETO

(75) Inventors: Jo Handelsman, Madison, WI (US); Robert M. Goodman, Madison, WI (US); Michelle R. Rondon, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 426 days.

(21) Appl. No.: 09/877,406

(22) Filed: Jun. 8, 2001

(65) Prior Publication Data

US 2002/0045177 A1 Apr. 18, 2002

Related U.S. Application Data

(63) Continuation of application No. 08/969,651, filed on Nov. 13, 1997, now Pat. No. 6,261,842, which is a continuation-in-part of application No. 08/956,692, filed on Oct. 24, 1997, now abandoned.

(60) Provisional application No. 60/063,230, filed on Oct. 23, 1997.

(51) Int. Cl.
*C12Q 1/68* (2006.01)
*C12N 1/12* (2006.01)
*C12N 1/20* (2006.01)
*C12N 15/00* (2006.01)
*C12N 5/00* (2006.01)

(52) U.S. Cl. .................... 435/6; 435/252.3; 435/325; 435/320.1; 435/471

(58) Field of Classification Search .......... 435/252.3, 435/325, 6, 320.1, 471
See application file for complete search history.

(56) References Cited

U.S. PATENT DOCUMENTS

| 5,783,431 A | 7/1998 | Peterson et al. |
| 5,824,485 A | 10/1998 | Thompson et al. |
| 5,958,672 A | 9/1999 | Short |
| 6,057,103 A * | 5/2000 | Short .................... 435/6 |

FOREIGN PATENT DOCUMENTS

| AT | O 468 220 A2 | 1/1992 |
| WO | WO 95/08548 | 3/1995 |
| WO | WO 95/33818 | 12/1995 |
| WO | WO 95/34646 | 12/1995 |
| WO | WO 97/12991 | 9/1996 |
| WO | WO 96/34112 | 10/1996 |
| WO | WO 96/40968 | 12/1996 |
| WO | WO 97/03202 | 1/1997 |
| WO | WO 97/04077 | 2/1997 |
| WO | WO 97/20918 | 6/1997 |
| WO | WO 97/20952 | 6/1997 |

OTHER PUBLICATIONS

Fuerst, R. In Frobisher & Fuerst's Micorbiology (1983), W.B. Saunders Company, Phildelphia, Chapter 2, pp. 14-22.*
Healy et al. (1994), *Direct Isolation of Genes from the Microbial Community of a Thermophilic Anaerobic Biomass Digester*, Abstr. Gen. Meet. Am. Soc. Microbiol. 94:366.
Schmidt et al. (1991), *Analysis of a Marine Picoplankton Community by 16S rRNA Gene Cloning and Sequencing*, J. Bacteriol. 173(14):4371.
Fuhrman et al. (1988), *Extraction from Natural Planktonic Microorganisms of DNA Suitable for Molecular Biological Studies*, Appl. Environ. Microbiol. 54:1426.
Carte (1993), *Marine Natural Products as a Source of Novel Pharmacological Agents*, Curr. Opin. Biotech. 4:275.
Smokvina, T. (1990), *Construction of a Series of pSAM2-Based Integrative Vectors for Use in Actinomycetes*, GENE 94(1):53.
Osburne et al. (1993), *An Assay for the Detection of Bacterial DNA Gyrase Inhibitors*, J. ANTIBIOT. 46(11):1764.
Brosch, R. et al. (1998), *Use of a Mycobacterium Tuberculosis H37Rv Bacterial Artificial Chromosome Library for genome Mapping, Sequencing and Comparative Genomics*, Infection and Immunity 66:21.
Ioannou, P. et al.. (1994), *A New bacteriophage P1-Derived Vector for the Propagation of Large Human DNA Fragments*, Nature Genetics, 6:84.
Kim, U.-J. et al. (1996), *Construction and Characterization of a Human Bacterial Artificial Chromosome Library*, GENOMICS, 34:213.
Liew, C. C. et al. (1994), *A618R Homo Sapiens cDNA Clone A618*, Proc. Natl. Acad. Sci. U.S.A., 91:10645.
Messerle, M. et al. (1997), *Cloning and Mutagenesis of a Herpesvirus Genome as an Infectious Bacterial Artificial Chromosome*, Proc. Natl. Acad. Sci. U.S.A., 94:14759.
Messerle, M. et al. (1996), *Reconstitution of a Recombinant Cytomegalovirus from Two Framents Cloned into Bacterial Artificial Chromosomes*, J. Mol. Med., 74:B08.
Ohmori, H. et al. (1995), *dinP, a New Gene in Escherichia coli, Whose Product Shows Similarities to UmuC and its Homologues*, Mutation Res. Lett., 347:1.
Primrose (1996), *Genomanalyse*, Spektrum Akademischer Verlag, 76.

(Continued)

Primary Examiner—James Ketter
Assistant Examiner—Konstantina Katcheves
(74) Attorney, Agent, or Firm—Joseph T. Leone, Esq.; DeWitt, Ross & Stevens S.C.

(57) ABSTRACT

The present invention provides methods and composition for accessing, in a generally unbaised manner, a diverse genetic pool for genes involved in biosynthetic pathways. The invention also provides compounds which can be identified by cloning biosynthetic pathways.

32 Claims, 7 Drawing Sheets

OTHER PUBLICATIONS

Szebenyi et al., *Insulin-Like Growth Factor II/Cation-Independent Mannose-6-Phosphate Receptor Precursor-Mouse*, XP-002104663 Abstract.

Shizuya, H. et al (1992), *Cloning and Stable Maintenance of 300-Kilobase-Pair Fragments of Human DNA in Escherichia coli*, Proc. Natl. Acad. Sci. U.S.A., 89:8794.

Woo, S. -S. et al (1994), *Construction and Characterization of a Bacterial Artificial Chromosome Library of Sorghum Bicolor*, Nucleic Acids Res., 22:4922.

Bintrim, S.B. et al. (1997), *Molecular Phylogeny of Archea from Soil*, Proc. Natl. Acad. Sci. USA 94:277.

Stein, J.L. et al. (1996), *Archael Ubiquity*, Proc. Natl. Acad. Sci. USA 93:6228.

Woese, C. et al. (1990), *Towards a Natural System of Organisms: Proposal for the Domains Archae, Bacteria, and Eucarya*, Proc. Natl. Acad. Sci. USA 87:4576.

Keeling, P.J. et al. (1994), *Archaebacterial Genomes: Eubacterial Form and Eukaryotic Content*, Curr. Opinion in Genetics and Devel. 4:816.

Sheng, Y. et al. (1995), *Transformation of Escherichia coli with Large DNA Molecules by Electroporation*, Nucleic Acids Res. 23(11):1990.

Jones, S. (1995), *An Update and Lessons from Whole-Genome Sequencing Projects*, Curr. Opin. in Gen. & Devel. 5:349.

Koonin, E.V. et al. (1996), *Sequencing and Analysis of Bacterial Genomes*, Curr. Bio. 6(4):404.

Fereyra, R.G. et al. (1993), *Cloning, Characterization, and Functional Expression in Escherichua coli of Chaperonin (groESL) Genes From the Phototropic Sulfur Bacterium Chromatium Vinosum*, J. of BACT. 175(5):1514.

Kawai, S. et al. (1993), *A Simple Method of Detecting Amplified DNA With Immobilized Probes on Microtiter Wells*, Analytic Biochem. 209:63.

Hancock, J.M. (1996), *Simple Sequences and the Expanding Genome*, BIOESSAYS 18(5):421.

He, H. et al. (1994), *Zwittermicin A, an Antifungal and Plant Protection Agent from Bacillus Cereus*, Tetrahedron Letters 35(16):2499.

Mahfuzur, S.R. et al. (1995), *Molecular Cloning of the IeuB Gene from Bacteroides Fragilis by Functional Complementation in Escheria coli*, Microbiol. Immun. 39(1):19.

Devine, K.M. et al. (1995), *Bacterial Genomes: a TIGR in the Tank*, TIG 11(11):429.

Cohen, S. (1993), *Bacterial Plasmids: Their Extraordinary Contribution to Molecular Genetics*, GENE 135:67.

Fonstein, M et al. (1995), *Physical Mapping of Bacterial Genomes*, J. of Bacteriology 177:3361.

Wang, M. et al. (1995), *Pulsed Field Separation of Large Supercoiled and Open-Circular DNAs and its Application to Bacteria Artificial Chromosome Cloning*, ELECTROPHORESIS 16:1.

Versalovic, J. et al. (1991), *Distribution of Repetitive DNA Sequences in Eubacteria and Application to Fingerprinting of Bacteria Genomes*, Nucleic Acids Research 19(24):6823.

Zhou. J. et al. (1996), *DNA Recovery from Soils of Diverse Composition*, Applied and Environ. Microbio. 62(2):316.

Matheson et al. (1997), *Development of Strain-Specific Probes*, Appl. Environ. Microbiol. 63:2864.

Wells, W.A. (1997), *Seeking Extremophiles*, INNOVATIONS 4(5):401.

Cole, S.T. et al. (1994), *Bacterial Genomics*, Fems Microbiol. Rev. 14:139.

Licitra, E. et al (1996),*A Three-Hybrid System for Detecting Small Ligand-Protein Receptor Interactions*, Proc. Natl. Acad. Sci. USA 93:12817.

Stein, J. et al., *Chracterization of Uncultivated Prokaryotes: Isolation and Analysis of a 40-Kilobase-Pair Genome Fragment from a Planktonic Marine Archaeon*, Journal of Bacteriology, Feb. 1996, p. 591-599.

Suzuki, M. et al., *Bacterial Diversity among Small-Subunit rRNA Gene Clones and Cellular Isolates from the Same Seawater Sample*, Applied and Enviornmental Microbiology, Mar. 1997, p. 983-989.

August, P.R. et al., *Sequence Analysis and Functional Characterization of the Violacein biosynthetic Pathway from Chromobacterium Violaceum*, J. Mol. Microbiol. Biotechnol (2000) 2(4): 513-519.

Beja, O. et al., *Bacterial Rhodopsin: Evidence for a New Type of Phototrophy in the Sea*, Science, 289, Sep. 2000, pp. 1902-1906.

Brady, S. et al., *Long-Chain N-Acyl Amino Acid Antibiotics Isolated from Heterologously Expressed Environmental DNA*, J. Am. Chem. Soc. 2000, 122, 12903-12904.

Brady, S. et al., *Cloning and Heterologous Expression of a Natural Product Biosynthetic Gene Cluster from eDNA*, Organic Letters, 2001, 3(13): 1981-1984.

Entcheva, P. et al., *Direct Cloning from Enrichment Culters, a Reliable Strategy for Isolation of Complete Operons and Genes from Microbial Consortia*, Applied and Environmental Microbiology, Jan. 2001, p. 89-99.

Fiandt, M., *Construction of an Environmental Genomic DNA Library from Soil Using the EpiFOS™ Fosmid Library Production Kit*, Epicentre Forum, vol. 7 No. 4, p. 6.

Henne, A. et al., *Construction of Environmental DNA Libraries in Escherichia coli and Screening for the Presence of Genes Conferring Utilization of 4-Hydroxybutyrate*, Applied and Environmental Microbiology, Sep. 1999, p. 3901-3907.

Henne, A. et al., *Screening of Environmental DNA Libraries for the Presence of Genes Conferring Lipolytic Activity on Escherichia coli*, Applied and Environmental Microbiology, Jul. 2000, p. 3113-3116.

Lorenz, P. et al., *Expression Cloning of Metagenome DNA from Soil*.

MacNeil, I.A. et al., *Expression and Isolation of Antimicrobial Small Molecules from Soil DNA Libraries*, J. Mol. Microbiol. Biotechnol. (2001) 3(2): 301-308.

Rondon, M. et al., *Toward Functional Genomics in Bacteria: Analysis of Gene Expression in Escherichia coli From A Bacterial Artificial Chromosome Library of Bacillus Cereus*, Proc. Natl. Acad. Sci. USA, vol. 96, pp. 6451-6455, May 1999.

Rondon, M, et al., *The Earth's Bounty: Assessing and Accessing Soil Microbial Diversity*, TIB Tech, Oct. 1999, vol. 17, pp. 403-409.

Rondon, M. et al., *Cloning the Soil Metagenome: a Strategy for Accessing the Genetic and Functional Diversity of Uncultured Microorganisms*, Applied and Environmental Microbiology, Jun. 2000, p. 2541-2547.

Wang, G. et al., *Novel Natural Products from Soil DNA Libraries in a Streptomycete Host*, Organic Letters, (2000) 2(16): pp. 2401-2404.

Beja, O. et al., *Construction and Analysis of Bacterial Artificial Chromosome Libraries From A Marine Microbial Assemblage*, Environmental Microbiology (2000) 2(5), pp. 516-529.

Osburne, M.S. et al., *Tapping into Microbial Diversity for Natural Products Drug Discovery*, ASM News, (2000) 66 (7), pp. 411-417.

*The Bugs That Live In Bugs*, The Economist, Aug. 31 (1996), pp. 65-67.

* cited by examiner

Advantages of the BAC vector system

- Based on the F factor of *E. coli*
- Low level of chimeric clones
- Stable maintenance of heterologous DNA sequences
- Stable maintenance of large inserts
- Easy to isolate and manipulate BAC plasmids
- Efficient transformation system of host

Uses of BAC libraries and clones

- Physical characterization of genomes (i.e. cloning, mapping, FISH, contig assembly)
- Direct sequencing from BACs is possible
- Complementation of mutants *in vivo*
- Introduction of gene fusions into cells

FIG. 2

BAC libraries

| Organism | Number of Clones | Average Insert Size (kb) |
|---|---|---|
| Sorghum | 13,440 | 157 |
| Rice | 11,000 | 125 |
| Bovine | 23,040 | 146 |
| *Arabidopsis thaliana* | 3,948 | 100 |
| Human | 96,000 | 140 |
| *Magnaporthe grisea* | 4,128 | 66 |
| *Arabidopsis thaliana* | 9,000 | 60 |
| Rice ssp. *japonica* | 7,296 | 150 |
| Rice ssp. *indica* | 14,208 | 130 |
| Human | 96,000 | 110 |
| Chicken | 4,416 | 390 |
| Lettuce | 50,000 | 111 |
| Barley | 10,750 | 95 |
| *Magnaporthe grisea* | 9,216 | 130 |

FIG. 3

Comparison of different library types

| vector type | insert size | 90%* | 99%* |
|---|---|---|---|
| plasmid | 5 kb | 2300 | 4600 |
| cosmid | 30 kb | 382 | 765 |
| BAC | 136 kb | 83 | 166 |

This is for a genome of 5 MB

* percent probability of library containing a specific sequence

FIG. 4

Expression of *Bacillus cereus* genes in *E. coli*

| Phenotype tested | Positive clones detected ? |
| --- | --- |
| Ampicillin resistance | YES (3) |
| Casein hydrolysis | NO |
| Citrate utilization | NO |
| Esculin hydrolysis | YES (1) |
| Hemolysis | YES (1) |
| Lecithin hydrolysis | YES (2) |
| RecA function | NO |
| Starch hydrolysis | NO |
| Tween 80 hydrolysis | NO |
| Zwittermicin A resistance | YES (2) |

FIG. 5

Heterologous expression of natural products pathways in Streptomyces species

| Compound | Class | Producer | Expressed in | Size of DNA |
|---|---|---|---|---|
| nikkomycin | peptidyl nucleoside | S. tendae | S. lividans | 31 plus 27 kb |
| puromycin | nucleoside | S. alboniger | S. lividans and S. griseus | 13 kb |
| actinorhodin | polyketide | S. coelicolor | S. parvulus | ~25 kb |
| cephamycin C | β-lactam | S. cattleya | S. lividans | 29 kb |
| 6-deoxy erythronolide B | polyketide | Saccharopolyspora erythraea | S. coelicolor | ~25 kb |

FIG. 6A

Heterologous expression of natural products pathways in E. coli

| Compound | Class | Producer | Size of DNA | Comments |
|---|---|---|---|---|
| pyrrolnitrin | phenylpyrrole | Pseudomonas fluorescens | <6.2 kb | Tac promoter used |
| herbicolin A-like compound | depsi-glycopeptide | Erwinia herbicola | | 170 kb native plasmid conjugated |
| violacein | modified amino acid | Chromobacterium violaceum | ~15 kb | also expressed in other Gram negative bacteria |

FIG. 6B

MICROORGANISM GENOMICS, COMPOSITIONS AND METHODS RELATED THERETO

RELATED APPLICATIONS

This application is a continuation of U.S. patent application Ser. No. 08/969,651 filed Nov. 13, 1997, now U.S. Pat. No. 6,261,842 which is a continuation-in-part of U.S. patent application Ser. No. 08/956,692 filed Oct. 24, 1997, now abandoned, which claims the benefit of U.S. Provisional Application Ser. No. 60/063,230 filed Oct. 23, 1997.

GOVERNMENT FUNDING

Work described herein was supported by funding from the National Institutes of Health. The United States Government has certain rights in the invention.

BACKGROUND OF THE INVENTION

Until recently, it was assumed that cultivation of microorganisms from the environment resulted in the isolation of a good proportion of the microorganisms present. Phylogenetic analysis of rRNA sequences obtained from direct sampling of environments has shown that this is not the case. Giovannoni et al. (1990) Nature 345:60–63; Pace et al. (1996) ASM News 62:463–470; Stahl et al. (1985) Appl. Environ. Microbiol. 49:1379–1384; Suzuki et al. (1997) Appl. Environ. Microbiol. 63:983–989; Ward et al. (1990) Nature 345:63–65. It is now apparent that the microorganisms that can be cultured from any environment using standard techniques probably represent the minority of the total species present in that environment, indicating that a vastly greater diversity of prokaryotes exists than suggested by culturing methods. Pace et al, supra; Stahl (1993) ASM News 59:609–613. The idea that perhaps the vast majority of bacteria in an environment are currently nonculturable has revolutionized thinking in microbiology, and has stimulated new approaches to the study of microbes. Woese et al. (1990) PNAS 87:4576–4579.

For instance, it is estimated that the number of species currently culturable from soil represents 1% or less of the total population. Griffiths et al. (1996) Microbial Ecol. 31:269–280; Torsvik et al. (1996) J. Ind. Microbiol. 17:170–178. DNA—DNA reassociation measurements have been used to determine total genetic diversity in one soil sample. The data indicated that greater than 4000 species might be present. Torsvik et al. (1990) Appl. Environ. Microbiol. 56:782–787. This represented at least 200 times more diversity than was observed by examining culturable bacteria from the same sample. Another study based on methods that did not involve culturing suggested 13,000 species in 100 g soil. Torsvik et al. (1994) p. 39–48, In Beyond the Biomass, K. Ritz, J. Dighton and K. E. Giller (eds.), John Wiley and Sons, Chichester. By estimating the total number of cells at $5 \times 10^{11}$ per gram of soil, this suggested an average of $5 \times 10^7$ cells per species assuming even species distribution. Thus even rare species might have fairly large population sizes in the soil. A recent analysis in our labs indicated that novel phyla of Bacteria and Archaea are present in soil. Bintrim et al. (1997) PNAS 94:277–282; Bintrim et al., in press. Of 144 cloned Bacterial 16S rRNA gene sequences examined, 45 had the closest affiliation to members of the phylum Proteobacteria, but of these clones, only 6 had close affiliation to known genera (Pseudomonas, Hafnia, Azospirillum). The clones were distributed across the entire Domain, and none were identical to any previously known sequence. Moreover, these studies revealed entirely new lineages of microbes in soil, both from the Domain Archaea and the Domain Bacteria. This indicates the enormous diversity of noncultured microorganisms from soil.

SUMMARY OF THE INVENTION

The present invention, in one aspect, provides methods and reagents for identifying genes from microbial organisms, the gene products of which are involved in biochemical transformation reactions that produce, for example, small organic molecules by de novo synthesis, or that chemically modify molecules ectopically provided in the microbe's environment. In general, the method provides host cells which have been engineered to express the opening reading frames of genomic DNA sub-cloned from a heterologous microorganism. The subject method detects changes in the phenotype of the host cell which are dependent on expression of open reading frames from the genomic DNA, e.g., which may be marked by altered biosynthetic capabilities.

Another aspect of the invention provides methods and reagents for identifying biosynthetic products, preferably other than those produced by ribosomal synthesis, which are generated by recapitulation of a heterologous microbial biosynthesis pathway in a host cell, or generated by a chimeric metabolic pathway involving both heterologous and endogenous gene products in the host cell. As above, the assay generally detects biochemical transformation reactions that produce, for example, small organic molecules by de novo synthesis, or that chemically modify molecules ectopically provided in the host microbe's environment. In general, the method provides host cells which have been engineered to express the opening reading frames of genomic DNA sub-cloned from a heterologous microorganism. Likewise, this embodiment of the subject method can be disposed to detect changes in the phenotype of the host cell which are dependent on the formation of a natural product, or the transformation of an ectopically added agent.

Thus, for example, there is provided a method for identifying a product of a biosynthetic pathway, comprising i) providing host cells containing a replicable vector including genomic DNA isolated from a source of uncultivated microrganisms, which host cells are provided under conditions wherein expression of open reading frame sequence(s) of the genomic DNA occurs; and ii) detecting a compound produced by the host cells, e.g., relative to host cells lacking the genomic DNA.

In another embodiment, the present invention provides a method for cloning genes of a biosynthetic pathway, comprising i) providing host cells containing a replicable vector including genomic DNA isolated from a source of uncultivated microrganisms, which host cells are provided under conditions wherein expression of open reading frame sequence(s) of the genomic DNA occurs; and ii) detecting the presence or absence of a biosynthetic pathway which is dependent on expression of at least one of the opening reading frames by the host microorganisms.

There is also provided a method for cloning genes of a biosynthetic pathway, comprising i) cloning, into a replicable vector, genomic DNA from a source of uncultivated microorganisms;

ii) expressing open reading frame sequence(s) of the genomic DNA in a host microorganism harboring the vector; and iii) detecting the presence or absence of a biosynthetic pathway which is dependent on expression of at least two of the opening reading frames by the host microorganism.

That method can also be used to identify a product of such a biosynthetic pathway produced in the host microorganism. In preferred embodiments, the biosynthetic pathway produces or transmutes a non-polymeric and/or non-proteinaceous compound. In certain preferred embodiments, the biosynthetic pathway produces a product having a molecular weight less than 7500 amu, more preferably less than 5000 amu, and even more preferably less than 2000 amu.

Yet another aspect provides a method for detecting a non-proteinaceous compound produced by a microorganism, comprising i) sub-cloning, into a replicable vector, genomic DNA from one or more uncultivated microrganisms;

ii) expressing open reading frame sequence(s) of the genomic DNA in a host microorganism harboring the vector;

iii) detecting ectopic production of a non-proteinaceous compound by the host microorganism.

In other embodiments, there is provided a method for cloning two or more genes encoding gene products functioning in a biological pathway of a microorganism, comprising i) sub-cloning, into a replicable vector, genomic DNA from one or more uncultivated microrganisms;

ii) expressing at least two open reading frame (ORF) sequences of the cloned genomic DNA in a cultivable host microorganism transfected with the vector;

iii) identifying ORF sequences which confer a phenotypic change on the host microorganism, which phenotypic change is dependent on the expression of at least two ORF sequences of the cloned genomic DNA.

In still other embodiments, there is provided a method for cloning genes encoding gene products functioning in the chemical transformation of a non-proteinaceous compound by a microorganism, comprising i) sub-cloning, into a replicable vector, genomic DNA from an uncultivated microrganisms;

ii) expressing open reading frame (ORF) sequence(s) of the cloned genomic DNA in a cultivable host microorganism transfected with the vector;

iii) detecting a phenotypic change of the host cell, which phenotypic change is dependent on the expression of at least two ORF sequences of the cloned genomic DNA.

iii) identifying one or more ORF sequence which confer a phenotypic change on the host cell, which phenotypic change is dependent on the chemical transformation of the non-proteinaceous compound.

In yet another embodiment, there is provided a method for identifying non-proteinaceous compounds produced by a uncultivated microorganisms, comprising i) generating a library of host microorganism transfected with a variegated population of vectors containing genomic DNA isolated from a sample of uncultivated microrganisms, which genomic DNA includes open reading frame (ORF) sequences which can be expressed from the vector in the host microorganism;

ii) culturing the transfected host microorganism under conditions wherein the ORFs are expressed;

iii) detecting ectopic production of non-proteinaceous compounds by the host microorganisms.

In preferred embodiments of the methods of the present invention, uncultivated mircoorganisms are prokaryotes. For instance, the microorganism can be *archaea* microorganism, such as *Crenarachaeota, Euryarchaeota,* or *Korachaeota.*

The mircoorganism(s) can be isolated from such sources as soil, insect intestines, plant rhizospheres, microbial mats, sulfur pools, marine samples and the like. One source of the microorganism is soil. Another source is environments of extreme pH (e.g., less than 1 or greater than 12) or temperature (e.g., greater than 80° C., or even greater than 100° C.).

In preferred embodiments, the sub-cloned genomic DNA is at least 25, 50, 75 or 100 kilobases in length.

The variegated population of vectors preferably include sub-cloned genomic DNA from at least 10, $10^3$, $10^4$ or even $10^5$ different microorganism species.

In preferred embodiments, the host microorganism is a species from the Bacteria, such as may be selected from the group consisting of *Acetobacter, Actinomyces, Aerobacter, Agrobacterium, Azotobacter, Bacillus, Bacteroides, Bordetella, Brucella, Chlamydia, Clostridium, Corynebacterium, Erysipelothrix, Escherichia, Francisella, Fusobacterium, Haemophilus, Klebsiella, Lactobacillus, Listeria, Mycobacterium, Myxococcus, Neisseria, Nocardia, Pasteurella, Proteus, Pseudomonas, Rhizobium, Rickettsia, Salmonella, Serratia, Shigella, Spirilla, Spirillum, Staphylococcus, Streptococcus, Streptomyces, Treponema, Vibrio,* and *Yersinia. Escherichia* and *Streptomyces* are most preferred.

In preferred embodiments, the vector is a low-copy number vector, such as a single-copy number vector.

BRIEF DESCRIPTION OF THE FIGURES

FIG. 2: Is a table illustrating advantages of utilizing BAC vector systems.

FIG. 3: is a table illustrating the average size inserts in various BAC libraries described in the art.

FIG. 4: compares the average insert for various library types.

FIG. 5: is a table describing the phenotypes confered on the host cell by the expression of the *Bacillus cereus* BAC library.

FIG. 6: is a table outlining the heterologous expression of natural products pathways in *Streptomyces* species.

DETAILED DESCRIPTION OF THE INVENTION

I. General Overview

Figure 1:
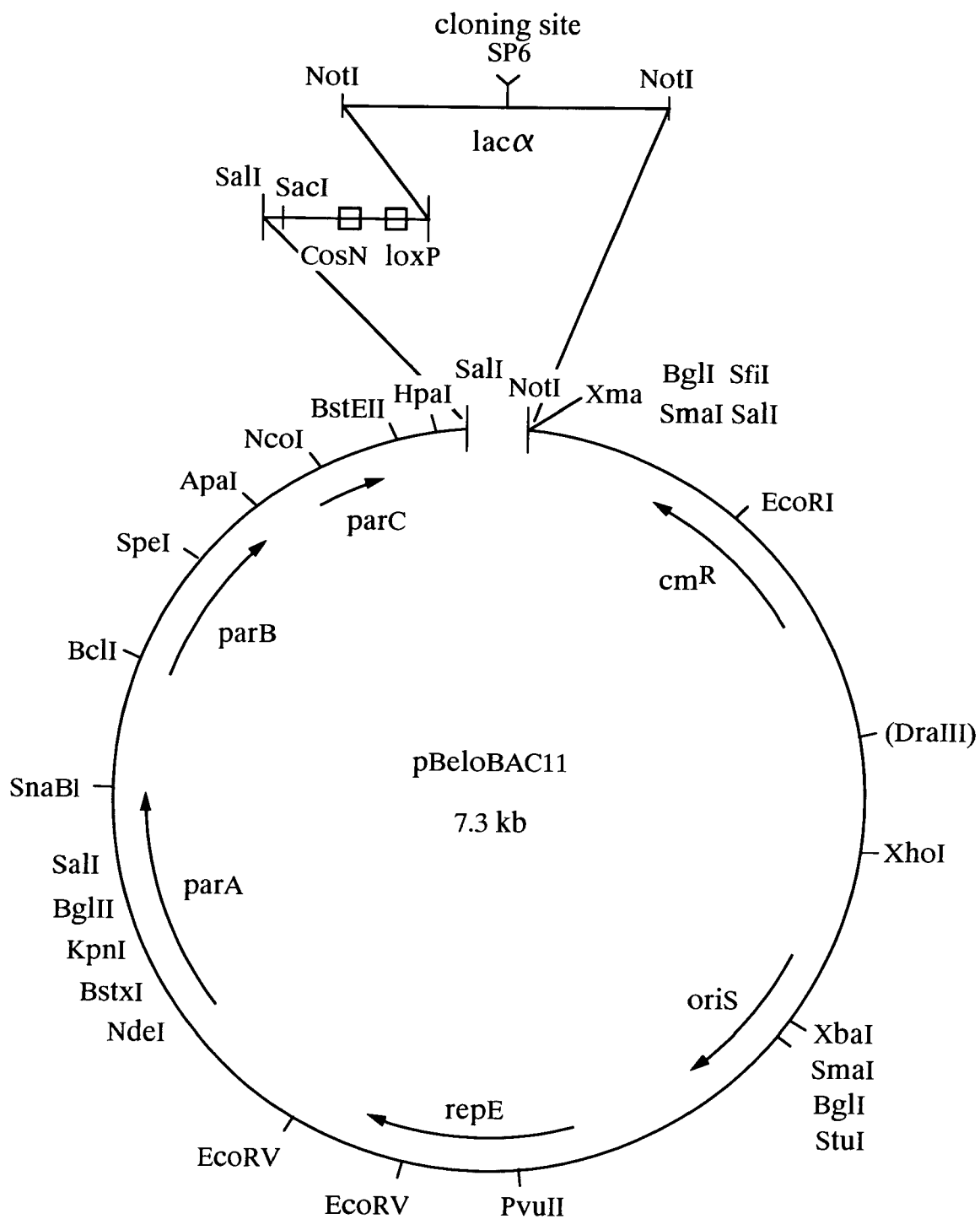
FIG. 1: pBeloBAC11 vector

Traditional methods of natural product discovery have relied on culturing microbes from the environment and implementing screens to test whether these cultured strains produce metabolites of interest. Franco et al. (1991) *Crit. Rev. Biotech.* 11:193–276. This has been a remarkably successful approach, but new detection methods as well as new source organisms are needed.

The present invention, in one aspect, provides methods and reagents for identifying genes from microbial organisms, the gene products of which are involved in biochemical transformation reactions that produce, for example, small organic molecules by de novo synthesis, or that chemically modify molecules ectopically provided in the microbe's environment. In general, the method provides host cells which have been engineered to express the opening reading frames of genomic DNA sub-cloned from a population of heterologous ("source") microorganisms. In general, the method begins with a variegated population of host cells engineered with the sub-cloned DNA, which in turn was isolated in a manner which greatly increases the complexity of the library by including genomes of hitherto unaccessed species of microorganisms. The subject method detects altered biosynthetic capabilities of the engineered host cells resulting from expression of open reading frames in the heterologous genomic DNA. The subject method takes a functional approach to screening the genomic libraries, requiring that the expression of the cloned genomic DNA recapitulates a biosynthetic pathway from the source organism, or combines with the gene products of the host organism to form a new chimeric pathway. This provides can provide a rapid and efficient means for cloning new genes of significant interest and identifying new biosynthetic products produced therefrom.

In samples from almost any environmental source, including those from extreme environments, one can generally find a widely diverse population of microorganisms, However, the microorganisms which are isolated by most standard culturing techniques are thought to represent only a tiny fraction of the total microorganisms in any environment. By eliminating initial culturing steps in the sub-cloning process, one of the salient features of the subject method is that it can be carried out in a manner which provides a relatively unbaised approach to cloning components of biosynthetic pathways. In this regard, the method can directly access the genetic material of a complex sample of microorganisms in a manner which can better preserve the phylogenetic diversity of the microorganism population in the subcloned DNA. Moreover, genomic sequences can be collected from microorganisms which exist only under extreme conditions, such as extreme temperatures or extreme pH's. This can greatly enhance the likelihood that novel biosynthetic pathways and their products can be identified.

For instance, one embodiment the subject method provides a means for cloning genes, preferably sets of two or more genes, whose expression products recapitulate a biosynthetic pathway of the source organism, or create chimeric biosynthetic pathways in a host cell. In general, the method includes a step of directly sub-cloning, into a replicable vector, genomic DNA isolated directly from an uncultivated sample of microrganism(s). A cultivable host microorganism is transfected with the resulting variegated population of vectors, and the transfected host cells are cultured under conditions wherein open reading frame (ORF) sequences of the cloned genomic DNA are expressed in the host cell. The generation of a new biosynthetic pathway in the host organism can be detected by any of a number of techniques involving, for example, chemical, photometric, biochemical and/or biological assay techniques for natural products. In this manner, the DNA of microorganisms which are difficult to culture, or are unculturable by current techniques, is now accessible and amenable to propagation and expression in organisms that are more easily cultured. Ths, such genetic information can be better represented in a functional genomics approach to identifying novel biosynthetic pathways.

Another aspect of the invention relates to the identification of the biosynthetic products, e.g., other than those produced by direct ribosomal synthesis, which can be produced by the recapitulation of heterologous biosynthetic pathways as describe above. As above, the assays for many natural producs are generally derived to detect biochemical transformation reactions that produce, for example, small organic molecules by de novo synthesis, or that chemically modify molecules ectopically provided in the host microbe's environment. In general, the method provides host cells which have been engineered to express the opening reading frames of genomic DNA sub-cloned from a heterologous polulation of microorganism, e.g., from a natural assemblage. As above, formation of a natural product, or the transformation of an ectopically added agent can be detected by assays utilizing chemical, photometric, biochemical and/or biologoical detection techniques.

It is not expected that every pathway provided in a library of cloned genomic DNA will recapitulate a functional pathway in the host cell; however, even if only a small number of the cloned pathways are expressed, the probability of discovering novel compounds remains high. To illustrate, a BAC library of 500,000 clones, each with an insert of at least 100 Kb, could include the genomes of 10,000 different microorganisms, given an average genome size of 5 Mb. This represents an enormous amount of genetic material available for analysis. Even if the frequency of heterologous expression of a pathway leading to a bioactive product is only in the range of 0.1 to 1%, there will be 500 to 5,000 clones with such an activity in a library of this size. This estimate is believed to be conservative given that at least 20% of culturable soil microorganisms produce antimicrobial metabolites and a reasonable proportion of genes from diverse microbes can be expressed in the system of the present invention.

Furthermore, the practice of the subject method can contribute to the basic understanding of microbial populations in nature. Current information on noncultured microbial communities is almost exclusively of a phylogenetic nature. While this is extremely powerful and important information, it does not provide a good measure of the physiological potential of these populations, as phylogeny is not a complete indicator of physiological diversity or metabolic capacity (Stahl et al. (1993) *ASM News* 59:609–613; and Stein et al. (1996) *J. Bacteriol.* 178:591–599). Thus, use of the subject approach of analyzing the physiological diversity of noncultured microbes can make significant contribution to basic research on microbial communities, which in turn has direct implications for understanding evolution and spread of infectious agents and antibiotic resistance genes.

II. Definitions

As used herein, the term "microorganism" includes prokaryotic and eukaryotic microbial species from the Domains *Archaea*, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the *Archaea*. The definitive difference between organisms of the *Archaea* and Bacteria domains is based on fundamental differences in the nucleotide base sequence in the 16S ribosomal RNA.

The term "*Archaea*" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the *Archaea* consist of two phylogenetically-distinct groups: *Crenarchaeota* and *Euryarchaeota*. On the basis of their physiology, the *Archaea* can be organized into three types: methanogens (prokaryotes that produce methane); extreme halophiles (prokaryotes that live at very high concentrations of salt ([NaCl]); and extreme (hyper) thermophilus (prokaryotes that live at very high temperatures). Besides the unifying *archaeal* features that distinguish them from Bacteria (i.e., no murein in cell wall, ester-linked membrane lipids, etc.), these prokaryotes exhibit unique structural or biochemical attributes which adapt them to their particular habitats. The *Crenarchaeota* consists mainly of hyperthermophilic sulfur-dependent prokaryotes and the *Euryarchaeota* contains the methanogens and extreme halophiles.

"Bacteria", or "Eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) *Proteobacteria*, e.g., Purple photosynthetic +non-photosynthetic Gram-negative bacteria (includes most "common" Gram-negative bacteria); (3) *Cyanobacteria*, e.g., oxygenic phototrophs; (4) *Spirochetes* and related species; (5) *Planctomyces;* (6) *Bacteroides, Flavobacteria;* (7) *Chlamydia;* (8) Green sulfur bacteria; (9) Green non-sulfur bacteria (also anaerobic phototrophs); (10) *Radioresistant micrococci* and relatives; (11) *Thermotoga* and *Thermosipho thermophiles.*

"Gram-negative bacteria" include *cocci,* nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium.*

The term "pathogen" is art recognized and refers generally to any organism which causes a deleterious effect on a selected host under appropriate conditions. Within the scope of this invention the term pathogen is intended to include fungi, bacteria, nematodes, viruses, viroids and insects.

"Gram positive bacteria" include *cocci,* nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "kb" refers to kilobases, e.g., thousands of contiguous nucleotide bases.

As used herein, the terms "gene" and "recombinant gene" refer to a nucleic acid sequence which is transcribed and (optionally) translated. Thus, a recombinant gene can comprise an open reading frame encoding a polypeptide. In such instances, the sequence encoding the polypeptide may also be referred to as an "open reading frame". In other embodiments, a gene can simply provide, on transcription, an antisense transcript, a ribozyme, or other RNA molecule which effects the phenotype of the host cell.

"Transfection", as used herein, refers to the insertion of an exogenous polynucleotide into a host cell, irrespective of the method used for the insertion, for example, direct uptake, transduction, mating or electroporation.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. On the other hand, "expression" of an antisense sequence or ribozyme will be understood to refer to the transcription of the recombinant gene sequence.

"Transcriptional regulatory sequence" is a generic term used throughout the specification to refer to DNA sequences, such as initiation signals, enhancers, and promoters, which induce or control transcription of a gene or genes with which they are operably linked.

By "operably linked" is meant that a gene and transcriptional regulatory sequence(s) are connected in such a way as to permit expression of the gene in a manner dependent upon factors interacting with the regulatory sequence(s).

The terms "host cells" and "recombinant host cells" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "PAC" is art recognized and refers to P1 artificial chromosomes.

The term "BAC" is art recognized and refers to bacterial artificial chromosomes

As used herein, a "reporter gene" is a gene whose expression may be assayed; reporter genes may encode any protein that provides a phenotypic marker, for example: a protein that is necessary for cell growth or a toxic protein leading to cell death, e.g., a protein which confers antibiotic resistance or complements an auxotrophic phenotype; a protein detectable by a colorimetric/fluorometric assay leading to the presence or absence of color/fluorescence; or a protein providing a surface antigen for which specific antibodies/ligands are available.

The term "biosynthetic pathway", also refered to as "metabolic pathway", refers to a set of anabolic or catabolic biochemical reactions for converting (transmutting) one chemical species into another. For instance, an antibiotic biosynthetic pathway refers to the set of biochemical reactions which convert primary metabolites to antibiotic intermediates and then to antibiotics.

The term "non-ribsomal synthesis" refers to a biosynthetic step or series of steps other than peptide bond formation in the translation of mRNAs into polypeptides. That is, the term refers to biosynthetic steps other than peptidyl transferase-catalyzed formation of peptide bonds. Likewise, "transformation of a non-proteinaceous compound" refers to the biochemical modification of a compound which is not directly produced by ribosome-mediated formation of peptide bonds "Ribosomal peptide synthesis", on the other hand, refers to ribosome-mediated formation of peptide bonds in the synthesis of polypeptide; though it does not include post-translational modification of the polypeptide by ribosome-independent reactions.

A "non-proteinaceous compound" refers to a compound which not produced by ribosome-mediated formation of peptide bonds. Thus the term includes the macrolide class of compounds and the like.

A "small molecule" refers to a compound which is not itself the product of gene transcription or translation (protein, RNA or DNA). Preferably a "small molecule" is a low molecular weight compound, e.g., less than 7500 amu, more preferably less 5000 amu and even more preferably less than 2500 amu. Examples of small molecules include, among the many compounds commonly referred to as "natural products", beta-lactam antibiotics, steroids, retinoids, polyketides, etc.

"Peptide antibiotics" are classifiable into two groups: (1) those which are synthesized by enzyme systems without the participation of the ribosomal apparatus, and (2) those which require the ribosomally-mediated translation of an mRNA to provide the precursor of the antibiotic.

The "non-ribosomal peptide" antibiotics are assembled by large, multifunctional enzymes which activate, modify, polymerize and in some cases cyclize the subunit amino acids, forming polypeptide chains. Other acids, such as aminoadipic acid, diaminobutyric acid, diaminopropionic acid, dihydroxyamino acid, isoserine, dihydroxybenzoic acid, hydroxyisovaleric acid, (4R)-4-[(E)-2-butenyl]-4,N-dimethyl-L-threonine, and ornithine can also be incorporated (Katz et al. (1977) *Bacteriological Review* 41:449–474; Kleinkauf et al. (1987) *Annual Review of Microbiology* 41:259–289). The products are not encoded by any mRNA, and ribosomes do not directly participate in their synthesis. Peptide antibiotics synthesized non-ribosomally can in turn be grouped according to their general structures into linear, cyclic, lactone, branched cyclopeptide, and depsipeptide categories (Kleinkauf et al. (1990) *European Journal of Biochemistry* 192:1–15). These different groups of antibiotics are produced by the action of modifying and cyclizing enzymes; the basic scheme of polymerization is common to them all. Non-ribosomally synthesized peptide antibiotics are produced by both bacteria and fungi, and include edeine, linear gramicidin, tyrocidine and gramicidin S from *Bacillus brevis*, mycobacillin from *Bacillus subtilis*, polymyxin from *Bacillus polymiyxa*, etamycin from *Streptomyces griseus*, echinomycin from *Streptomyces echinatus*, actinomycin from *Streptomyces clavuligerus*, enterochelin from *Escherichia coil*, gamma-($\alpha$-L-aminoadipyl)-L-cysteinyl-D-valine (ACV) from *Aspergillus nidulans*, alamethicine from *Trichoderma viride*, destruxin from *Metarhizium anisolpliae*, enniatin from *Fusarium oxysporum*, and beauvericin from *Beauveria bassiana*. Extensive functional and structural similarity exists between the prokaryotic and eukaryotic systems, suggesting a common origin for both. The activities of peptide antibiotics are similarly broad, toxic effects of different peptide antibiotics in animals, plants, bacteria, and fungi are known (Hansen (1993) *Annual Review of Microbiology* 47:535–564; Katz et al. supra; Kleinkauf et al. supra; Kolter et al. (1992) *Annual Review of Microbiology* 46:141–163).

The "aminoglycosides" and other "carbohydrate-containing" antibiotics refer to organic molecules derived at least part from a saccharide or polysaccharide. For instance, the aminoglycosides are oligosaccharides consisting of an aminocyclohexanol moiety glycosidically linked to other amino sugars. Streptomycin, one of the best studied of the group, is produced by *Streptomyces griseus*. Streptomycin, and many other aminoglycosides, inhibits protein synthesis in the target organisms.

The "ribosomally-synthesized peptide" antibiotics are characterized by the existence of a structural gene for the antibiotic itself, which encodes a precursor that is modified by specific enzymes to create the mature molecule.

The term "variegated population" refers to a population of, e.g., cells, vectors, or the like, including multiple different species. A variegated population of cells preferably includes at least $10^2$, $10^3$, $10^4$ or $10^5$ different phenotypes in the cell population. Likewise, a variegated population of vectors preferably includes at least $10^2$, $10^3$, $10^4$ or $10^5$ different vectors.

III. Sources for Microbial Cellular DNA

As set out above, the methods of the present invention will allow access to the microbial genetic information present in an environment, particularly those having complex microbial communities, without requiring knowledge of any particular organism or the ability to culture it. The microorganisms from which recombinant genomic libraries may be prepared include prokaryotic microorganisms, such as eubacteria and *archaea*, and lower eukaryotic microorganisms such as fungi, some algae and protozoa. The subject methods are based, in part, on the understanding that non-cultured microbes can constitute the vast majority of the total microbes in any environment, including heavily sampled environments such as soil (for a review, see Amann et al. (1995) *Microbiol. Rev.* 59:143–169).

In preferred embodiments, the libraries of genomic DNA ultimately sampled in the present method are can be produced by directly sub-cloning genomic DNA from a complex microbial sample without an intervening step of culturing cells from the sample. In techniques requiring an intermediate culturing steps, populations of micoroorganism can be lost due the inability of any single culture conditions to uniformity propagate cells in a complex mixture of microorganisms. The DNA recovered in the subject method is understood to be relatively unbaised in this respect. Sources, for example, of microbes from which the genomic library clones are obtained include, but are not limited to, such environmental samples as may be isolated from soil, insect intestines, plant rhizospheres, microbial mats, sulfur springs, ocean and fresh water ecosystems, etc. In certain embodiments, the genomic DNA can be obtained from extreme environments, such as from samples of arctic or antarctic ice, water or permafrost sources, samples from environments of extreme pH (acidic or basic), samples from volcanic origins or other high temperature and/or high sulfur environments, samples from soil or plant sources of tropical origin, and the like. Each of the above sample sources are representative of meaningful environments that can be exploited by the subject method as each likely contains a great population of unculturable microorganisms or unculturable combinations of microorganisms. Moreover, many of these environments have not been heavily examined for natural products, etc. The microbial source from which genomic DNA is to be isolated preferably includes at least 100 different microorganisms, more preferably at least $10^3$, and even more preferably at least $10^4$, $10^5$ and even $10^6$ different microorganisms.

To further illustrate, many invertebrates have been shown to have a diverse collection of microbes associated with their digestive systems. See, for example, Amann et al. (1995) *Microbiol. Rev.* 59:143–169. The microbes in these environments are phylogenetically diverse and physically accessible. For example, termite intestines contain representatives of the *proteobacteria, spirochetes, bacteroides* and low G+C Gram-positive groups, as well as members that may represent novel bacterial and *archaeal phyla* altogether (Ohkuma et al. (1996) *Appl. Environ. Microbiol.* 62:461–468). The population of gut microbes is often rich in microbes which are unculturable by existing methods; therefore an approach that does not rely on culturing should be successful in gaining access to the genetic information of these microbes. Advantages of obtaining DNA samples from this environment include the fact that the genes of a large proportion of these microbes may be easy to express in *E. coli* and the like, since many gut microbes are proteobacteria, the same metabolically diverse phylum to which *E. coli* belongs.

In another embodiment, genomic DNA can be isolated from microorganisms present in soil (land or marine). Soil microbes have been an unparalleled source for natural product discovery based on conventional approaches. Moreover, Applicants' work has revealed that a wide range of previously unaccessed microbes exist in soil samples (Bintrim et al. (1997) *PNAS* 94:277–282; Bintrim et al., *in press*). It is expected, for example, that genomic DNA from a range of different bacteria, *archaea* and other microbes can be isolated from various soil samples, and the majority of that DNA is expected to be from previously uncultured microbes.

At the microscopic scale, soil is extremely heterogeneous and consists of numerous microenvironments that differ in many chemical and physical properties. To access the microbial diversity of soils, microbiologists have long relied on standard microbial cultivation techniques. However, the microbes that were cultivated from soil, as a whole, indicated neither the abundance nor the phylogenetic diversity in situ. It is estimated that fewer than 1% of the microbes observed by microscopy are generally recovered by cultivation under standard conditions. Applicants understand that the difference between microflora counted by cultivation and that observed by direct microscopy is largely due to the presence in soil of a vast and as yet uncharacterized taxonomic diversity which are not readily accessible by presently available culturing techniques. The instant methods, by utilizing direct DNA isolation techniques independent of microbial cultivation, can be well suited for the general cloning of genomic DNA from soil microflora.

A number of approaches can be taken to prepare DNA from soil microbes and the like, including: direct isolation, and separation of microbial cells from the environmental support followed by cell lysis and DNA purification. The first method maximizes the amount and diversity of DNA recovered, the second method will maximize the size of recovered DNA. Preferably the isolation and lysis methods, e.g., as described below, will result in lysis of a wide variety of microbial cell types so as to minimize species loss at this step. However, depending on the protocol, it will be understood that selectivity can be introduced at such steps. For example, the method described in the appended examples for the isolation of genomic DNA from *Bacillus cereus* is not expected to yield significant fungal DNA contamination, since fungal cells will not be lysed by this method. Depending on the host cell, minimization of eukaryotic DNA in the samples can increase the "productivity" of the library, e.g., since bacterial genes are more likely to be expressed in the prokaryotic host cell.

To explain by example, in one embodiment of a direct isolation protocol, a soil sample is mixed with extraction buffer and treated with protease and SDS. The mixture is centrifuged and the supernatant is extracted, e.g., with chloroform. The DNA is precipitated, such as with isopropanol, and purified on a low melting-point agarose gel or the like.

However, in preferred embodiments the subject method relies on the isolation of microbes from the source sample, such as soil, followed by extraction of genomic DNA from the isolated microbes. In the present invention, microbial isolation followed by DNA purification, rather than direct extraction of DNA from the source sample, e.g., soil, is designed to facilitate the isolation of very high molecular weight DNA from the sample. Microbes can be isolated directly from soil samples using previously developed methods applicable to a variety of soils and which provide maximum diversity. See, for example, O'Donnell et al., In C. Edwards (ed.), *Monitoring Genetically Manipulated Microorganisms in the Environment*, John Wiley and Sons, Chichester; Smith et al. (1994) In K. Ritz, J. Dighton and K. E. Giller (eds.), *Beyond the Biomass*, John Wiley and Sons, Chichester.

In either embodiment, to isolate the genomic DNA, the microbial cells must be lysed. To that end, a variety of means are available for lysing recalcitrant organisms. For example, a common method for the mechanical lysis of fungi requires the sample to be alternately vortexed with glass beads and cooled in an ice bath. The cellular extract is recovered by centrifugation after puncturing the bottom of the tube. Similarly, a Mini-Beadbeater TM has been used for lysing bacterial and *archaeal* species, where cells are ruptured by vigorous shaking with phenol and zirconium beads. See, Hurley, et al. (1987) *J Clin Micro*, 25:2227–2229.

Methods for lysis of soil bacteria have included multiple cycles of freeze-thawing, and passage through a French press, which is a high-pressure shearing device. One recent method for lysing these bacteria calls for the successive application of sonication, microwave heating, and thermal shocks. See, Picard, et al. (1992) *Applied and Environmental Microbiology*, 58:2717–2722.

Another common approach for lysis of microorganisms has involved enzymes that attack the cell walls. For example, lyticase has proven effective in lysing fungi, while achromopeptidase, mutanolysin, or proteinase K removes cell walls from most Gram-positive microorganisms. See, e.g., Kaneko et al., (1973) *Agr. Biol. Chem.*, 37:2295–2302; Bollet, et al. (1991) *Nucleic Acids Research* 19:1955; Siegel et al. (1981) *Infection and Immunity* 31:808–815.

However, in preferred embodiments, to construct the large insert DNA libraries, the microbes are first embedded in agarose plugs or microbeads. The agarose acts as a solid yet porous matrix which allows for the diffusion of various reagents for DNA purification and subsequent manipulations while preventing the DNA from being sheared. In some instances, microbeads are preferred over plugs because the use of beads increases the surface area surrounding the sample by approximately 1000 fold thereby allowing for more efficient and rapid diffusion of chemicals and enzymes into and out of the agarose beads. Once embedded, the cells are lysed and proteins degraded in the presence of, e.g., 0.5 M EDTA, 1% sarcosyl, and 0.1–1.0 mg/ml of proteinase-K. After cell lysis and protein degradation, the remaining DNA is suitable for enzymatic modifications.

In an illustrative embodiment, a soil sample can be homogenized or shaken in buffer to disperse soil clumps. The sample is then treated with a mild detergent and/or cation-exchange resin to dissociate microbial cells from soil particles (O'Donnell et al., supra). Microbes are then separated from the soil by differential centrifugation. Final purification of microbes can be by density gradient centrifugation or aqueous two-phase partitioning (O'Donnell et al., supra). As described in the appended examples, recovery of in excess of 40%–60% of the total microbe diversity of the sample can be achieved using these methods. These microbial preparations will be the source of DNA for construction of the library.

In another embodiment, flow cytometry techniques can be used to isolate microorganisms from biological and non-biological debris with which they may be associated in an intial sample, e.g., before lysing the cells to isolate genomic DNA. See, for example, Davey et al. (1996) *Microbiol Rev*

60:641; and Porter et al. (1997) *Soil Biol Biochem* 29:91. Flow cytometry has provided means for the rapid detection, identification, and separation of cells, including microbes. The cells can be identified, e.g., by fluorescence activated cell sorting (FACS) techniques, by detecting an endogenous autofluorescence which many cells possess (e.g., because of phycobiliproteins or other pigments), or by detecting the presence of a FACS-detectable vital stain. Vital stains are, e.g., those which penetrate living and dead cells at different rates. For example, brilliant cresyl blue or trypan blue may be used. Which ever method is used to isolate cells by flow cytometry will preferably be carried out in a manner which is indiscriminate for the type of cell. For example, Gram-negative bacteria absorb positively charged stains and Gram-positive bacteria absorb negatively charged stains. Thus, either a single stain which stains both cell-types, or a cocktail of stains which stains both cell-types should be used.

Flow cytometry methods and equipment are well known in the art and readily adpated for use in the subject assay. In recent years, optical/electronic instrumentation for detecting fluorescent labels on or in cells has become more sophisticated. For example, flow cytometry can be used to sort cells at a rate exceeding 25,000 cells per second. These instruments can excite fluorescence at many wavelengths of the UV, visible, and near IR regions of the spectrum In some instances, unusual amounts of endogenous nucleases can aggravate the problem of recovering intact nucleic acids. For example, one of the few groups that has successfully extracted intact DNA from *Trichomonas vaginalis* reports that this organism is characterized by a high level of endogenous nuclease activity, and that its DNA is unusually susceptible to degradation during isolation. See, Riley, et al. (1992) *J. Clin. Microbiol.* 30:465–472. However, broad spectrum protease and nuclease inhibitors can be used to inhibit the activity of these enzymes with regard to fragmentation of genomic DNA samples.

In general, the isolation of genomic DNA from a source of microorganisms can be carried out with any appropriate technique which yields high molecular weight DNA, e.g., with an average length of at least 25 kb, more preferably with an average length of at least 50 kb, and even more preferably with an average length of at least 75 or 100 kb. Procedures which may be used include agarose gel electrophoresis, pulsed field gel electrophoresis, density gradient centrifugation and fluoresence activated sorting. In addition to providing suitably sized fragments of genomic DNA, the fractionation step can also be designed to facilitate separation of the DNA from potential inhibitors of enzymatic reactions.

To illustrate, in one embodiment genomic DNA isolated from the sample cells is size fractionated using a pulsed field gel electrophoresis protocol. Pulsed field gel electrophoresis (PFGE) is capable of resolving a wide size range of DNA molecules which would all co-migrate in conventional agarose gels. The art, for example, describes pulsed field gel conditions which permit DNA fragments of up to 250 kilobases (kb) to be separated. Birren et al. (1993) in *Pulsed Field Gel Electrophoresis*. Academic Press, San Diego; and Birren et al. (1994) *Nucleic Acids Res* 22:5366–70. The separations, which can employ commercially available gel boxes, can be achieved using conditions which have been described for traditional pulsed field conditions. With DNA fragments of several hundred kb and smaller, higher field strengths may be used, resulting in still greater increases in separation speed.

In another illustrative embodiment, DNA samples can be enriched for high molecular weight fragments by flow cytometry-based separation techniques. Several flow cytometry protocols are known in the art, and provide ultrasensitive fluorescence detection technique which can be adapted to the subject method for sizing large DNA fragments, e.g., up to about 175 kb in length. In one technique, fluorescence bursts are recorded as individual, dye-stained DNA fragments pass through a low power, focused, continuous laser beam. The magnitudes of the fluorescence bursts are linearly proportional to the lengths of the DNA fragments. This method has been demonstrated to be well suited to characterizing PAC/BAC clones and can be adapted for use in the enrichment of large inserts for the subject libraries. Huang et al. (1996) *Nucleic Acids Res* 24: 4202–9.

To further illustrate, genomic DNA can be isolated from cells immobilized in agarose plugs. The DNA can be partially digested in situ and run into a pulsed field gel for isolation, e.g., using a GeneNavigator System (Pharmacia Biotech). The DNA fragments can be size-selected to control the average insert size, and in certain embodiments will preferably be selected for sub-cloning from samples DNA from 100 to 500 kb in length. Protocols for enzymatic manipulation of DNA have been developed for digestion, modification, and ligation of DNA in gel slices (Birren et al. (1994) *Nucleic Acids Res* 22:5366–70). The enriched DNA can then be cloned into a suitable vector, such as the BAC vector pBeloBAC11, and introduced into the host strain, e.g., by electroporation (Kim et al. (1996) *Genomics* 34:213–218; and Shizuya et al. (1992) *PNAS* 89:8794–8797). The average insert size of the clones can be determined by the analysis of multiple clones. In many embodiments, it will be useful to use multiple different restriction enzymes for the cloning procedure, and in particular to use two enzymes, such as HindIII and BamHI, which have recognition sequences that differ in GC content. The GC content of the DNA in the sample is expected to vary, and digestion conditions will be chosen to maximize representation in the library of DNAs with different GC content.

With further regard to assembling genomic DNA constructs, where genomic fragments of sub-optimal length are initially isolated, the method of "chromosomal building" can be used to create longer fragments. This method allows rapid construction of large pieces of defined DNA in F factor-based vectors. The method relies on a combination of general and site-specific recombination to join large pieces of DNA from smaller, overlapping cloned segments in vivo.

Additionally, the practitioner can get an estimate of the phylogenetic diversity represented by the DNA cloned in the library by screening for rRNA sequences from, e.g., specific phyla of Bacteria or *Archaea*. Clones can be pooled into groups and DNA prepared from the pools. Then PCR amplification of rRNA sequences will be accomplished with primers specifically hybridizing to rRNA sequences of a given phylogenetic group, but not to *E. coli* rRNA sequences (Amann et al. (1995) *Microbiol. Rev.* 59:143–169; Manz et al. (1996) *Microbiology* 142:1097–1106). The presence of rRNA genes from organisms of different phyla will indicate that the library contains DNA from diverse sources. This kind of analysis will be useful to determine, for example, that DNA from a diverse range of microorganisms was cloned.

IV. Expression Vectors

The library of genomic clones can be prepared, as described above, without the need for culture expansion, amplification or other supplementary procedures. The resulting genomic DNA sequences are ligated into vectors suitable for maintenance of large DNA sequences in the desired host cell. In addition to stable maintenance of the large genomic fragments, the choice of vector is also greatly influenced by the requirement that all, or substantially all, of the protein coding sequences (open reading frames) present in the genomic fragment be transcribable from the vector in the host cell. To this end, the vector may include transcriptional regulatory sequences operably linked to the genomic insert so as to promote or enhance expression of at least a portion of the heterologous coding sequences. However, it is more likely that expression of the recombinant genes will rely on transcriptional activation by the endogenous regulatory sequence of the genomic insert. In either circumstance, the tertiary structure of the resulting vector should provide access for transcriptional factors and polymerase complexes, in the host cell, to at least a substantial portion of the genomic insert. Moreover, the vector will preferably include at least one origin of replication which is functional in the host cell, as well as one or more selectable marker genes for maintenance of the vector.

Representative examples of vectors which may be used include viral vectors, phage, plasmids, phagemids, cosmids, phosmids, bacterial artificial chromosomes (BACs), bacteriophage P1, P1-based artificial chromosomes (PACs), yeast artificial chromosomes (YACs), yeast plasmids, and any other vectors suitable for a specific host cell and capable of stably maintaining and expressing a genomic DNA insert of at least 20 kb, and more preferably greater than 50–75 kb.

Standard recombinant DNA techniques involve the in vitro construction of plasmid and viral chromosomes that can be transformed into host cells and clonally propagated. These cloning systems, whose capacities for exogenous DNA range up to 50 kilobase pairs (kb), are well suited to the analysis and manipulation of small gene clusters from organisms in which the genetic information is tightly packed, as is the case with many microbes. It is increasingly apparent, however, that many of the functional genetic units of interest may span enormous tracts of DNA.

Preferred vectors for the present invention are the so-called artificial chromosomes. One feature of these vectors is their ability to carry large genetic inserts, e.g., greater than 50 kb, with enough mitotic and meiotic stabilities to make their genetic manipulation straightforward. P1 and PAC/BAC clones can contain high molecular weight inserts (75–100 kb or 120+ kb); about four to six times larger than Lambda, and two to three times larger than Cosmids. In addition, the low copy number of the P1, PAC or BAC vector, e.g., in a restriction and recombination-deficient *E. coli* host, confer vastly improved stability on these clones. The upper limit on the size of the insert is often great enough that thousands of genes can be included on one vector. Thus, a single vector could provide, through inclusion of gene clusters, all the genes to a specific biosynthetic pathway.

P1-based artificial chromosomes (PACs) and bacterial artificial chromosomes (BACs) have significantly expanded the size of fragments from eukaryotic genomes that can be stably cloned in *E. coli* and the like as plasmid molecules. Advantages of these system include the low copy number of the vector (based on the single copy F plasmid of *E. coli*), large possible insert size (clones containing inserts of up to 300 Kb have been propagated), stability of clones in vivo, high cloning efficiency, and easy manipulation of clones by standard techniques (Shizuya et al. (1992) *PNAS* 89:8794–8797). See also FIG. 2. The BAC and PAC systems provide a method to construct a stable library of large inserts, which in certain instances can be critical to the success of the subject method. See FIGS. 3 and 4. Large inserts may needed, for example, because a biosynthetic gene cluster(s) of interest may be large, and because large insert size will maximize the total genetic material represented in the library. Biosynthetic genes for secondary metabolites, for example, are in most cases clustered in one region of the chromosome, along with the genes for self-resistance and pathway-specific regulatory genes. Thus, it is probable that entire pathways can be cloned in one large DNA fragment (Vining et al. (1995) *Genetics and Biochemistry of Antibiotic Production*, Butterworth-Heinemann, Boston), including the genes required to confer resistance on the host. Additionally, secondary metabolites are usually made from simple primary metabolites, such as amino acids, acetate, or common sugars. Many of these building blocks are likely to be present in the *E. coli* cell. Expression of even a tiny fraction of cloned genes will mean success for this project in terms of the discovery of novel compounds.

The utility of the BAC and PAC systems in large-scale genomic mapping efforts has led to the development of protocols optimized specifically for these plasmids with large inserts (Birren et al. (1993) in *Pulsed Field Gel Electrophoresis*. Academic Press, San Diego; Sheng et al. (1995) *Nucl. Acids Res.* 23:1990–1996; and Wang et al. (1995) *Electrophoresis* 16:1–7), and be readily adapted to construction of BAC and PAC libraries of microbial DNA. Moreover, genes from diverse prokaryotes such as *Thermotoga, Synechocystis, Chromatium, Clostridium, Lactobacillus, Corynebacterium, Bacteroides,* and *Leptospira* can be expressed in *E. coli* either from their own promoters or from promoter-like sequences present within the cloned DNA. See, for example, Black et al. (1995) *J. Bacteriol.* 177:1952; Buysens et al. (1996) *Appl. Environ. Microbiol.* 62:865; Chavez et al. (1995) *Plant Mol. Biol.* 28:173; DeLong et al. (1992) *PNAS* 89:5685; and Ding et al. (1993) *J. Gen. Microbiol.* 139:1093; Ferreyra et al. (1993) *J. Bacteriol.* 175:1514. These species represent seven different phyla of bacteria, and demonstrate that a very wide diversity of heterologous gene expression signals can be utilized in such host cells as *E. coli*. Highly efficient gene expression (including transcriptional, translational, and post-translational processes) will obviously not occur in all cases. There will be unavoidable selections and limitations introduced in the manipulation and expression of genetic material isolated directly from the environment. However, purely on stochastic grounds, the vast microbial diversity in the sampled environment means that many genes will be successfully expressed.

In preferred embodiments, the subject method utilizes cloning vectors that are based on the *E. coli* F-factor replicon. This features allows for strict copy number control of the clones so that they are stably maintained at 1–2 copies per cell. The stability of the cloned DNA during propagation in an *E. coli* host cell is substantially higher in lower copy number vectors than in multi-copy counterparts (Kim et al, *NAR* 20:1083–1085). The stabilizing effect of BAC and Fosmid vectors is notable especially for certain genomic DNA that are normally unstable in high copy number vectors. This includes genomes of *Archaeal* origins.

As an exemplary embodiment, the present method utilizes the pBeloBAC11 vector. See, FIG. 1, and, for example, Zimmer et al. (1997) *Genomics* 42:217–226; and Cai et al. (1995) *Genomics* 29:413–425. The pBeloBAC11 vector represents the second generation BAC cloning vectors, which was developed from the pBAC108L by introducing the LacZ gene to facilitate recombinant identification with blue and colorless (white) phenotypes. pBeloBAC11 is a mini-F factor based plasmid. There are three unique cloning sites: Bam HI, SphI, and Hind III, which are flanked by the T7 and SP6 promoters. These promoters can facilitate generating RNA probes for chromosome walking and DNA sequencing of the insert fragment at the vector-insert junction. The G+C rich restriction sites (Not I, Eag I, Xma I, Sma I, Bgl I, and Sfi I) can be used to excise the inserts of BAC clones. There are two selective markers for cloning purposes: LacZ gene for recombinant selection and CMR (chloramphenicol) for transformant selection. The F factor codes for genes that are essential to regulate its own replication and controls its copy number in a cell. The regulatory genes include oriS, repe, parA, and parB. The oriS and repe mediate the unidirectional replication of the F factor, and the parA and parB maintain copy number at a level of one or two per cell. BAC libraries are generated by ligating size-selected restriction digested DNA with pBeloBAC11 followed by, for example, electroporation into E. coli. This vector allows lacZ-based positive color selection of the BAC clones that have insert DNA in the cloning sites at the time of library construction.

The construction of BAC libraries using pBeloBAC11 can be carried out by any of number of ways. Merely for illustration, the vector is first digested with HindIII, Bam H1 or SphI and then dephosphorylated to prevent self ligation. Next, high molecular weight DNA is partially digested with HindIII, Bam H1 or SphI, or linkers containing such sites are added as flanking sequences thereto, and size-selected DNA are ligated into the vector. The vector can then electroporated into appropriate host cells. Recombinant transformants are selected on media containing chloramphenicol, X-Gal, and IPTG. After recombinant transformants are detected, their size can be assayed by a simple plasmid DNA minipreparation followed by digestion with NotI to free the DNA insert from the vector, and CHEF electrophoresis. The most widely used E. coli strain for BAC cloning is DH10B (Hanahan, (1983) J. Mol. Biol. 166:557–580). Key features of this strain include mutations that block: 1) restriction of foreign DNA by endogenous restriction endonucleases (hs-dRMS); 2) restriction of DNA containing methylated DNA (5' methyl cytosine or methyl adenine residues,and 5' hydroxymethyl cytosine) (mcrA, mcrB, mcrC, and mrr); 3) recombination (recA1).

Another family of vectors which can be used in the subject method are the PAC vectors. The PAC vectors have most of the features of the BAC system however the vectors contains the SacB gene which provides a positive selection for recombinant clones during library construction. SacB encodes sucrose synthase. When cells are grown in the presence of saccharose, sucrose synthase will degrade saccharose into levan which is highly toxic to E. coli. The BamHI cloning site is within the SacB gene and thus disruption of the SacB gene by insertion of a large DNA fragment allows for growth of the cell on media containing saccharose. Additionally the vector has a "pUC19-link", containing a high copy number origin of DNA replication, which is used for convenient vector propagation and is later removed during vector preparation for library construction.

Still another suitable BAC vector is the pFOS1 vector, which is a single copy cosmid vector constructed by fusing pBAC108L and pUCcos (a pUC vector in which the region including lacZ and multiple cloning sites was replaced by lambda cos sequence). In vivo homologous recombination between two vectors via cos sites resulted in pFOS1. The vector is extremely unstable in most of E. coli strains due to the presence of double cos sites. pop2136 strain (Methods in Enzymology vol. 152 pp173–180, 1987), for no apparent reason, can maintain pFOS1 (and other double-cos cosmid vectors) with some stability. The bireplicon is driven by the pUC replication origin, and exists in high copies in E. coli. After in vitro packaging and transfection to E. coli, the structure of Fosmids is exactly the same as pBAC108L clones except the size; therefore Fosmids are mini-BACs with 40 kb inserts. Fosmid library can easily be constructed using the protocol for constructing cosmid libraries with double-cos vectors. The Fosmid system is useful for quickly generating miniBAC libraries from small amounts of source DNA, such as flow-sorted chromosomal DNA.

The subject vectors will generally contain a selectable marker gene. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. As set out above, the pBeloBAC11 vector includes a gene providing chloramphenicol resistance for transformant selection.

In certain instances, it may be desirable to express the genomic orfs in a eukaryotic cell, such as a fungal host cell. Functional characterization of genes within a given PAC or BAC clone can be carried out by transferring the DNA into eukaryotic cells for transient or long-term expression. To facilitate transfection studies, the vector can be engineered to include a marker gene which is selectable in the eukaryotic host cell. These retrofitting protocols may be applied with a number of markers of interest to extend the functionality of PAC and BAC libraries, and specialized aspects of such manipulation of E. coli-based artificial chromosomes are outlined in, for example, Mejia et al. (1997) Genome Res 7:179–86.

The vector should, as pointed out above, include at least one origin of replication for the host cell into which the vector is to be transfected. If also necessary, the vector can include one or more copy-control sequence for controlling the number of copies of the vector in any one cell. By way of illustration, for use in E. Coli and other bacterial host cells, the vector preferably includes one or more bacterial origins of replication (Ori), and preferably ones which do not adversely affect gene expression in infected cells. For example, the bacterial Ori can be a pUC bacterial Ori relative (e.g., pUC, colEI, pSC101, p15A and the like). The bacterial origin of replication can also, for example, be a RK2 OriV or f1 phage Ori. The vectors also further inlcude a single stranded replication origin, such as an f1 single-stranded replication origin.

The vector is transfected into and propagated in the appropriate host. Methods for transfecting the host cells with the genomic DNA vector can be readily adapted from those procedures which are known in the art. For example, the genomic DNA vector can be introduced into the host cell by such techniques as the use electroporation, precipitation with DEAE-Dextran or calcium phosphate, or lipofection.

To further illustrate the use of BAC vectors in the subject method, the following exemplary protocols can be followed or readily adapted for use with most any BAC vector system of the subject method.

A). Preparation of BAC Vector DNA

Because BAC vectors are single copy plasmids, it can be difficult in certain instances to obtain large amounts of BAC vector DNA. Extra care may also be needed to minimize the contamination of DNA from the host cell that consists more than 99% of the total DNA. However, following such procedures as provided below, it is possible to obtain sufficient quantitities of BAC vector DNA (e.g., a few micrograms of pBeloBAC11) from liter cultures. The exemplary procedures are described for E. Coli host cells, though the protocol can be readily adapted for a variety of other host cells.

1) Starting from a single colony, grow E. coli strain containing pBeloBAC11 vector in 3 liters of LB+chloramphenicol (15 ug/ul) with good aeration overnight. Make sure to take a blue colony on an X-gal/IPTG plate.
2) Harvest the cells by centrifugation, and resuspend the cell pellet in Solution I (without lysozyme). Use 25 ml Solution I per liter culture.
3) Add lysozyme to 2.5 mg/ml, and mix by inversion.
4) Add Solution II (50 ml per liter culture) and mix well by inversion. Leave on ice for 10 minutes.
5) Add 37 ml of Solution III per liter culture. Mix gently by swirling. Keep on ice for 10 minutes.
6) Centrifuge 30 minutes at 8,000 g or higher at 4° C.
7) Decant the supernatant and filter it through several layers of cheesecloth. Add the RNase to a final concentration of 0.1 mg/ml, and incubate at room temperature for 15–30 minutes.
8) Using 4 Qiagen-tip 500, pre-purify the supernatant as instructed by the Qiagen procedure. Qiagen tips are pre-equilibrated with QBT, then the supernatant is applied, then washed with large volumes of QC, and eluted by 15 ml of QF per column.
9) Precipitate the DNA by adding 0.7 volume of isopropanol, mix, and centrifuge 15,000 xg for 30 minutes at 4° C.
10) Wash the DNA pellet with ice cold 70% ethanol, and air dry.
11) Resuspend DNA in 18.6 ml of TE Add 20.5 g CsCl and dissolve. This is to be spun in two tubes in Beckman 70.1 Ti rotor.
12) Add 0.4 ml of EtBr (10 mg/ml), mix and perform ultracentrifugation for 2–3 days at 45,000 rpm in a Beckman 70.1 Ti rotor.
13) Two bands should be visible under U.V. Isolate the lower band, extract with isoamylalcohol 3–4 times, and dialyze for a few hours in TE at 4° C.
14) Ethanol precipitate DNA, rinse the pellet with 70% ethanol, and dissolve DNA pellet in TE, and store at −20° C. Solution I: 25 mM TrisHCl, pH 8.0; 50 mM Glucose Solution II: 0.2 N NaOH; 1% SDS Solution III: 5 M Potassium Acetate, pH 4.8. Add glacial acetic acid to a solution of 3 M potassium acetate to achieve a pH 4.8.

B). Preparation of Source DNA. Ligation and Electroporation

BAC Ligation

DNA should be in low melting agarose, in TAE or stored in 0.05 M EDTA. Dialyze the sample in 50 ml tube at 4° C. against 1×TE, 1×PA for 3–5 hr with one change of solution. Melt agarose at 65° C. for 10 minutes, transfer tube to 44–45° C. water bath. Add agarase, using about 1.5 U for each 100 μl of melted gel. Digest 1 hour at 45° C.

Set up ligation with an approximate molar ratio of vector to insert of 10:1. Every time a new batch of DNA is used it is a good idea to set up trial ligations with varying amounts of vector given the difficulties of determining the concentration of insert DNA with certainty.

A typical reaction would contain 100 ng insert DNA with an average size of 200 kb and 36.5 ng vector in a volume of between 120 and 150 μl.

Reaction Mixture: 100 μl DNA, 1.8 μl pBAC (20 ng/ml), 2.0 μl 10× ligation buffer, 2.0 μl 10×PA, 0.5 μl ligase 400 U/μl, 3.7 μl H$_2$O Combine insert DNA, vector, PA, and H$_2$O. Heat 5 minutes at 65° C., cool on ice. Add ligase buffer and enzyme. Mix by slowly stirring contents. Incubate overnight at 16° C.

After ligation, carry out drop-dialysis of sample against approximately 25 ml 0.5×TE, 1×PA for 2 hours at room temperature in a 100 mm petri dish. 1×PA is a mixture of spermine and spermidine which has a combined concentration of 1 mM (Spermidine-4HCl MW 254.6, Spermine-3HCl MW 348.6). Dissolve both in water, filter sterilize. Store frozen aliquots at −20° C. [100× stock=Spermidine 75 mM (0.19 g/10 ml)+Spermine 30 mM (0.104 g/10 ml); 1000× stock=Spermidine 750 mM (1.9 g/10 ml)+Spermine 300 mM (1.04 g/10 ml)]

Preparation of Competent Cells and BAC Electroporation

1) Inoculate flasks of SOB (without Mg++) by diluting a fresh saturated (overnight) culture of DH10B 1:1000 (i.e., 0.3 ml to a flask containing 300 ml medium).
2) Grow with shaking at 37° C. until OD550 reaches 0.7 (no higher than 0.8). This should take approximately 5 hr when shaken at 200 rpm.
3) Harvest cells by spinning in GSA rotor for 10 minutes at 5,000 rpm.
4) Resuspend pellet in a volume of 10% sterile glycerol equal to the original culture volume.
5) Spin 10 minutes at 5,000 rpm at 4° C.
6) Carefully pour off supernatant (pellet will be quite loose) and resuspend cells again in 10% glycerol equal to the original culture volume.
7) Spin 10 minutes at 5,000 rpm at 4° C.
8) Carefully pour off supernatant, resuspend cells in the volume of glycerol remaining in the centrifuge bottle. Pool the cells in one small centrifuge tube.
9) Spin 10 minutes at 7,000 rpm in SS34 rotor.
10) Pour off supernatant and resuspend cells in 10% glycerol, using a volume of 2.0 ml per liter of initial culture.
11) Aliquot to microfuge tubes (100–200 μl per tube) and freeze quickly in a dry ice-ethanol bath. Store cells at −70° C.

Electroporation

1) Wash and UV sterilize cuvettes, place on ice and prepare culture tubes with 0.5 ml SOC.
2) Thaw cells and aliquot 25–30 μl to microfuge tubes on ice.
3) Add 1–3 μl of ligation mix, and gently mix by flicking tube bottom with finger.
4) Transfer to cuvette and wipe cuvette dry.
5) Electroporate using settings of 100 Ohms, 2.5 kV, and 25 μFa. This usually gives a time constant of approximately 2.4 msec.
6) Immediately rinse contents of cuvette with SOC and transfer to culture tube using a sterile Pasteur pipet.
7) Shake for 45 minutes at 37° C. Spread on LB plates containing 12.5 μg/ml chloramphenicol, 50 μg/ml×Gal and 25 μg/ml IPTG.

C). Purification of BAC DNA Via Mini-Preps

A major advantage of working with BAC clones is the ease with which pure BAC DNA can be isolated via mini-prep methods. Alkaline lysis is superior to boiling methods, producing higher yields with greater reproducibility, though a significant amount of the DNA may be nicked by the alkaline treatment and converted from supercoiled to open circular molecules. While the low copy number of BACs means that relatively much less DNA is recovered than from multi-copy vectors, sufficient DNA can be obtained from a few ml of bacterial culture for restriction analysis, hybridization, FISH or PCR. Because the BACs are supercoiled, they are resistant to shear-induced breakage during the isolation, hence even BACs as large as 350 kb require no extraordinary measures in handling the DNA. Although vortexing should be avoided, the miniprepped DNA, it may be pipetted using regular pipet tips without any detectable damage to the DNA.

Alkaline lysis mini-preps of BAC DNA can be performed by the following steps. Unless stated, pauses or incubations are not needed between each step. Typical yield of BAC DNA from 3 ml cultures is 100–200 ng.

1) Inoculate a colony into a 10 ml culture containing 1.5 ml LB+ 12.5 $\mu$g/ml chloramphenicol.
2) Grow overnight at 37° C. by shaking at 200 rpm.
3) Transfer the culture to a 1.5 ml microfuge tube.
4) Pellet the cells by spinning at full speed in a microfuge for 30 seconds, and aspriate or pour off growth medium.
5) Thoroughly resuspend the cell pellet in 100 $\mu$l chilled Solution I using a pipetman.
6) Place the tubes on ice and add 200 $\mu$l of freshly prepared Solution II. Cap the tube, mix by inversion 8–10 times and return tubes to ice. At this stage the cells will lyse and the solution will grow clear and viscous.
7) Add 150 $\mu$l of Solution III. Cap tube, mix by inversion 8–10 times and return to ice. The addition of solution III will cause the formation of a flocculent precipitate.
8) Centrifuge for 6 minutes at room temperature at full speed in a microfuge.
9) Transfer the supernatant by pouring to a new microfuge tube. Any visible debris that is transferred can be removed with a toothpick or pipet tip.
10) Precipitate the DNA by adding 1 ml room temperature 100% ethanol and mixing by inversion.
11) Centrifuge for 6 minutes at room temperature in a microfuge.
12) Pour off the supernatant and rinse the pellet by adding 500 $\mu$l of room temperature 70% ethanol.
13) Pour off the ethanol and drain the tube by resting it upsidedown on a paper towel. Allow to dry completely.
14) Resuspend in 201 $\mu$l TE.

Solution 1: 25 mM TrisHCl pH 8.0 50 mM Glucose 10 mM EDTA After cells have been resuspended, add Lysozyme to 2.5 mg/ml Solution 2: 0.2N NaOH 1% SDS Solution 3: 5M Potassium Acetate pH 4.8 This is a tricky solution to prepare. It is made by adding glacial acetic acid to a solution of 3M potassium acetate to achieve a pH of 4.8. This is accomplished by adding a minimal amount of water to the potassium acetate and then adding the acetic acid until the potassium acetate is dissolved and the pH has reached 4.8.

V. Host Cells

The ideal host strain will be one with the following characteristics: permissive for replication and maintenance of the genomic DNA vector; lack of endogenous natural products that would be active in the screens; high transformation efficiency; ability to express heterologous genes from sequences within the insert, and presence of appropriate precursor molecules needed for a biosynthetic pathway created by the expression of the recombinant genomic sequences. Given these requirements, a preferred host cell is *E. coli*. One particularly useful strain is the *E. coli* DH10B as a host, since this is the optimal host for cloning large DNA fragments from foreign sources (Sheng et al. (1995) *Nuc. Acids Res.* 23:1990–1996). Since most BAC libraries have been constructed in DH10B, cloning protocols have been optimized for this strain (Sheng et al., supra; and Birren et al. (1994) *Nuc. Acids Res.* 22:5366–5370).

Although *E. coli* can be used as the host, it will be appreciated by those skilled in the art that a much broader selection of host cells exist. For instance, once a quantitative assessment of the microbial fauna of an environmental sample has been made, the practioner will be able to identify the more abundant taxa. Based on this information, other expression systems and host cells can be used to build further genomic expression libraries. For example, if it were found that actinomycetes is an abundant group in a noncultured soil community, then an attempt to maximize the range of expression of genes from environmental DNA could include constructing a BAC system in *Streptomyces*. These bacteria are amenable to molecular genetic techniques and are a proven source of antibiotics based on culturing, but are substantially different from *E. coli* in terms of gene expression and thus, may support production of compounds not possible using *E. coli* as the host. This approach can be complementary to the *E. coli* system.

Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescens*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* DH5 alpha , and *E. coli* W3110 (ATCC 27,325) are suitable. These examples are illustrative rather than limiting.

In certain embodiments, the host strain can be engineered to lose the function of certain genes, and the ability of a genomic clone to complement the loss-of-function being assayed for in the detection step.

In still other embodiments, where the source of the genomic DNA is very diverse from the host cell, the host cell can be engineered to express transcription factors, polymerase subunits, etc, cloned from the organisms representing the source of the genomic DNA. For instance, an *E coli* cell can be engineered to express genes involved in gene expression in *Archaea* with the goal of increasing the level of expression of the *archaeal* genomic DNA provided in the foreign cell.

VI. Detection Techniques

The ability to detect formation of a new, functional biochemical pathway in the host cell is important to the practice of the subject methods. In general, the assays are carried out to detect heterologous biochemical transformation reactions of the host cell that produce, for example, (small) organic molecules and the like as part of a de novo synthesis pathway, or by chemical modification of molecules ectopically provided in the host cell's environment. The presence of generation of such molecules by the host cell can be detected in "test extracts", e.g., which may be conditioned media, cell lystates, cell membranes, or semipurified or purified fractionation products thereof. The latter may be, as described above, prepared by classical fractionation/purification techniques, including chromatographic separation, or solvent fractionation (e.g., methanol ethanol, acetone, ethyl acetate, tetrahydrofuran (THF), acetonitrile, benzene, ether, bicarbonate salts, dichloromethane, chloroform, petroleum ether, hexane, cyclohexane, diethyl ether and the like). Where the assay is set up with a responder cell, e.g., to test the effect of an activity produced by the host cell on a whole cell rather than a cell fragment, the host cell and test cell can be co-cultured together (optionally separated by a culture insert, e.g., Collaborative Biomedical Products, Catalog #40446).

In certain embodiments, the assay will be set up to directly detect, e.g., by chemical or photometric techniques, a molecular species which is produced (or destroyed) by a biosynthetic pathway of the recombinant host cell, e.g., whose production or degradation is dependent at least in part on expression of the heterologous genomic DNA. In other embodiments, the detection step of the subject method involves characterization of fractionated media/cell lysates (the test extract), or application of the test extract to a biochemical or biological detection system. In other embodiments, the assay indirectly detects the formation of products of a heterologous pathway by observing a phenotypic change in the host cell, e.g., in an autocrine fashion, which is dependent on the establishment of a heterologous biosynthetic pathway in the host cell.

In certain embodiments, analogs related to a known class of compounds will be sought, as for example analogs of alkaloids, aminoglycosides, ansamacrolides, beta-lactams (including penicillins and cephalosporins), carbapenems, terpinoids, prostanoid hormones, sugars, fatty acids, lincosaminides, macrolides, nitrofurans, nucleosides, oligosaccharides, oxazolidinones, peptides and polypeptides, phenazines, polyenes, polyethers, quinolones, tetracyclines, streptogramins, sulfonamides, steroids, terpinoids, vitamins and xanthines. In such embodiments, if there is an available assay for directly identifying and/or isolating the natural product, and it is expected that the analogs would behave similarly under those conditions, the detection step of the subject method can be as straight forward as directly detecting analogs of interest in the cell culture media or preparation of the cell. For instance, chromatographic or other biochemical separation of a test extract can be carried out, and the presence or absence of an analog detected, e.g., spectrophotometrically, in the fraction in which the known compounds would occur under similar conditions. In certain embodiments, such compounds can have a characteristic fluorescence or phosphorescence which can be detected without any need to fractionate the media and/or recombinant cell.

In related embodiments, whole or fractionated culture media or lysate from a recombinant host cell can be assayed by contacting the test sample with a heterologous cell ("test cell") or components thereof. For instance, a test cell, e.g., which can be prokaryotic or eukaryotic, is contacted with conditioned media (whole or fractionated) from a recombinant host cell, and the ability of the conditioned media to induce a biological or biochemical response from the target cell is assessed. For instance, the assay can detect a phenotypic change in the target cell, as for example a change in: the transcriptional or translational rate or splicing pattern of a gene; the stability of a protein; the phosphorylation, prenylation, methylation, glycosylation or other post translational modification of a protein, nucleic acid or lipid; the production of $2_{nd}$ messengers, such as cAMP, inositol phosphates and the like. Such effects can be measured directly, e.g., by isolating and studying a particular component of the cell, or indirectly such as by reporter gene expression, detection of phenotypic markers, and cytotoxic or cytostatic activity on the test cell.

When screening for bioactivity of test compounds produced by the recombinant host cells, intracellular second messenger generation can be measured directly. A variety of intracellular effectors have been identified. For instance, for screens intended to isolate compounds, or the genes which encode the compounds, as being inhibitors or potentiators of receptor- or ion channel-regulated events, the level of second messanger production can be detected from downstream signalling proteins, such as adenylyl cyclase, phosphodiesterases, phosphoinositidases, phosphoinositol kinases, and phospholipases, as can the intracellular levels of a variety of ions.

The following examples describe assay formats for natural products which effect receptor or ion channel function. However, they also provide general guidance for detecting the effects of a test sample on other cellular functions.

Thus, in one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach*. G. Milligan, Ed. Oxford University Press, Oxford England). When compounds that modulate cAMP are tested, it will be possible to use standard techniques for cAMP detection, such as competitive assays which quantitate [$^3H$]cAMP in the presence of unlabelled cAMP.

Certain receptors and ion channels stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In various cells, specific proteases are induced or activated in each of several arms of divergent signaling pathways. These may be independently monitored by following their unique activities with substrates specific for each protease.

In the case of certain receptors and ion channels, it may be desirable to screen for changes in cellular phosphorylation. Such assay formats may be useful when the receptor pathway of interest is a receptor kinase or phosphatase. For example, immunoblotting (Lyons and Nelson (1984) *Proc. Natl. Acad. Sci. USA* 81:7426–7430) using anti-phosphotyrosine, anti-phosphoserine or anti-phosphothreonine antibodies. In addition, tests for phosphorylation could be also useful when the targeted receptor itself may not be a kinase, but activates protein kinases or phosphatase that function downstream in the signal transduction pathway.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the S. cerevisiae pheromone signaling pathway is comprised of a protein kinase cascade composed of the products of the STE11, STE7, and FUS3/KSS1 senes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

In yet another embodiment, the targeted signal transduction pathway upregulates expression or otherwise activates an enzyme which is capable of modifing a substrate which can be added to the cell. The signal can be detected by using a detectable substrate, in which case lose of the substrate signal is monitored, or altenatively, by using a substrate which produces a detectable product. In preferred embodiments, the conversion of the substrate to product by the activated enzyme produces a detectable change in optical characteristics of the test cell, e.g., the substrate and/or product is chromogenically or fluorogenically active. In an illustrative embodiment the signal transduction pathway causes a change in the activity of a proteolytic enzyme, altering the rate at which it cleaves a substrate peptide (or simply activates the enzyme towards the substrate). The peptide includes a fluorogenic donor radical, e.g., a fluorescence emitting radical, and an acceptor radical, e.g., an aromatic radical which absorbs the fluorescence energy of the fluorogenic donor radical when the acceptor radical and the fluorogenic donor radical are covalently held in close proximity. See, for example, U.S. Pat. Nos. 5,527,681, 5,506,115, 5,429,766, 5,424,186, and 5,316,691; and Capobianco et al. (1992) Anal Biochem 204:96–102. For example, the substrate peptide has a fluorescence donor group such as 1-aminobenzoic acid (anthranilic acid or ABZ) or aminomethylcoumarin (AMC) located at one position on the peptide and a fluorescence quencher group, such as lucifer yellow, methyl red or nitrobenzo-2-oxo-1,3-diazole (NBD), at a different position near the distal end of the peptide. A cleavage site for the activated enzyme will be diposed between each of the sites for the donor and acceptor groups. The intramolecular resonance energy transfer from the fluorescence donor molecule to the quencher will quench the fluorescence of the donor molecule when the two are sufficiently proximate in space, e.g., when the peptide is intact. Upon cleavage of the peptide, however, the quencher is separated from the donor group, leaving behind a fluorescent fragment. Thus, activation of the enzyme results in cleavage of the detection peptide, and dequenching of the fluorescent group.

In still other embodiments, the detectable signal can be produced by use of enzymes or chromogenic/fluorscent probes whose activities are dependent on the concentration of a second messenger, e.g., such as calcium, hydrolysis products of inositol phosphate, cAMP, etc. For example, the mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) Environ Health Perspect 84:45–56). As an exemplary method of Ca++ detection, cells could be loaded with the Ca++ sensitive fluorescent dye fura-2 or indo-1, using standard methods, and any change in Ca++ measured using a fluorometer.

As certain embodiments described above suggest, in addition to directly measuring second messenger production, the signal transduction activity of a receptor or ion channel pathway can be measured by detection of a transcription product, e.g., by detecting receptor/channel-mediated transcriptional activation (or repression) of a gene(s). Detection of the transcription product includes detecting the gene transcript, detecting the product directly (e.g., by immunoassay) or detecting an activity of the protein (e.g., such as an enzymatic activity or chromogenic/fluorogenic activity); each of which is generally referred to herein as a means for detecting expression of the indicator gene. The indicator gene may be an unmodified endogenous gene of the host cell, a modified endogenous gene, or a part of a completely heterologous construct, e.g., as part of a reporter gene construct.

In one embodiment, the indicator gene is an unmodified endogenous gene. For example, the instant method can rely on detecting the transcriptional level of such endogenous genes as the c-fos gene (e.g., in mammalian cells) or the Bar1 or Fus1 genes (e.g., in fungal cells) in response to such signal transduction pathways as originating from G protein coupled receptors.

Many reporter genes and transcriptional regulatory elements are known to those of skill in the art and others may be identified or synthesized by methods known to those of skill in the art. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368); β-lactamase or GST.

Transcriptional control elements for use in the reporter gene constructs, or for modifying the genomic locus of an indicator gene include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (cAMP Responsive Element) found to the 5' of promoters known to be responsive to elevated cAMP levels. Upon binding of phosphorylated CREB to a CRE, transcription from this promoter is increased.

Phosphorylation of CREB is seen in response to both increased cAMP levels and increased intracellular Ca levels. Increased cAMP levels result in activation of PKA, which in turn phosphorylates CREB and leads to binding to CRE and transcriptional activation. Increased intracellular calcium levels results in activation of calcium/calmodulin responsive kinase II (CaM kinase II). Phosphorylation of CREB by CaM kinase II is effectively the same as phosphorylation of CREB by PKA, and results in transcriptional activation of CRE containing promotors.

Therefore, a transcriptionally-based readout can be constructed in cells containing a reporter gene whose expression is driven by a basal promoter containing one or more CRE. Changes in the intracellular concentration of Ca++ (a result of alterations in the activity of the receptor upon engagement with a ligand) will result in changes in the level of expression of the reporter gene if: a) CREB is also co-expressed in the cell, and b) either an endogenous or heterologous CaM kinase phosphorylates CREB in response to increases in calcium or if an exogenously expressed CaM kinase II is present in the same cell. In other words, stimulation of PLC activity may result in phosphorylation of CREB and increased transcription from the CRE-construct, while inhibition of PLC activity may result in decreased transcription from the CRE-responsive construct.

Continuing with the illustrative example, the marker gene is coupled to the receptor signaling pathway so that expression of the marker gene is dependent on activation of the receptor. This coupling may be achieved by operably linking the marker gene to a receptor-responsive promoter. The term "receptor-responsive promoter" indicates a promoter which is regulated by some product of the target receptor's signal transduction pathway.

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of fungal cells, suitable positively selectable (beneficial) genes include the following: URA3, LYS2, HIS3, LEU2, TRP1; ADE,1, 2, 3, 4, 5, 7, 8; ARG1, 3, 4, 5, 6, 8; HIS1, 4, 5; ILV1, 2, 5; THR1 ,4; TRP2, 3, 4, 5; LEU1, 4; MET2, 3, 4, 8, 9, 14, 16, 19; URA1, 2, 4, 5, 10; HOM3, 6; ASP3; CHO1; ARO 2, 7, CYS3; OLE1; INO1,2,4; PRO1,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In other embodiments, the reporter gene can be used to detect agents from the test samples which can directly alter the activity of a transcription factor or other DNA associated protein. For instances, the detection step can be used to identify compounds from the test samples which can inhibit or potentiate transcription of a gene by a cellular or viral transcription factor.

In still other embodiments, the detection step is provided in the form of a cell-free system, e.g., a cell-lysate or purified or semi-purified protein or nucleic acid preparation. The samples obtained from the recombinant host cells can be tested for such activities as inhibiting or potentiating such pairwise complexes (the "target complex") as involving protein-protein interactions, protein-nucleic acid interactions, protein-ligand interactions, nucleic acid-nucleic acid interactions, and the like. The assay can detect the gain or loss of the target complexes, e.g., by endogenous or heterologous activities associated with one or both molecules of the complex.

Assays which are performed in cell-free systems, such as may be derived with purified or semi-purified proteins, are often preferred as "primary" screens in that they can be generated to permit rapid development and relatively easy detection of an alteration in a molecular target when contacted with a test sample. Moreover, the effects of cellular toxicity and/or bioavailability of the test sample can be generally ignored in the in vitro system, the assay instead being focused primarily on the effect of the sample on the molecular target as may be manifest in an alteration of binding affinity with other molecules or changes in enzymatic properties (if applicable) of the molecular target. Detection and quantification of the pairwise complexes provides a means for determining the test samples efficacy at inhibiting (or potentiating) formation of complexes. The efficacy of the compound can be assessed by generating dose response curves from data obtained using various concentrations of the test sample. Moreover, a control assay can also be performed to provide a baseline for comparison. For instance, in the control assay conditioned media from untransformed host cells can be added.

The amount of target complex may be detected by a variety of techniques. For instance, modulation in the formation of complexes can be quantitated using, for example, detectably labelled proteins or the like (e.g. radiolabelled, fluorescently labelled, or enzymatically labelled), by immunoassay, or by chromatographic detection.

Additionally, the effect of a test sample on a target complex can be determined by use of a an interaction trap assay. See, for example, U.S. Pat. No. 5,283,317; PCT publication WO94/10300; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696). The interaction trap assay relies on reconstituting in vivo a functional transcriptional activator protein from two separate fusion proteins, one of which comprises the DNA-binding domain of a transcriptional activator fused to one of the proteins of the target complex. The second fusion protein comprises a transcriptional activation domain (e.g. able to initiate RNA polymerase transcription) fused to the other protein of the target complex. When the two protein interact, the two domains of the transcriptional activator protein are brought into sufficient proximity as to cause transcription of a reporter gene. Thus, test samples which are able to inhibit or potentiate interaction of the fusion proteins will result in modulation of the expression of the reporter gene. Versions of the interaction trap assay also exist for detecting protein-nucleic acid and nucleic acid-nucleic acid interactions and be readily adapted for use in the subject method.

In still other embodiments, a purified or semi-purified enzyme can be used as to assay the test samples. The ability of a test sample to inhibit or potentiate the activity of the enzyme can be conveniently detected by following the rate of conversion of a substrate for the enzyme.

In yet other embodiments, the detection step can be designed to detect a phenotypic change in the host cell which is induced by products of the expression of the heterologous genomic sequences. For instance, the assay can detect the ability of a genomic clone to confer antibiotic resistance to the host cell. Many of the above-mentioned cell-based assay formats can also be used in the host cell, e.g., in an autocrine-like fashion.

In addition to providing a basis for isolating biologically active molecules produced by the recombinant host cells, the detection step can also be used to identify genomic clones which include genes encoding biosynthetic pathways of interest. Moreover, by interative and/or combinatorial subcloning methods relying on such detection steps, the individual genes which confer the detected pathway can be cloned from the larger genomic fragment.

The subject screening methods can be carried in a differential format, e.g., comparing the efficacy of a test sample in a detection assay derived with human components with those derived from, e.g., fungal or bacterial components. Thus, selectivity as an bacterocide or fungicide can be a criteria in the selection protocol.

The host strain need not produce high levels of the novel compounds for the method to be successful. Expression of the genes may not be optimal, global regulatory factors may not be present, or metabolite pools may not support maximum production of the product. The ability to detect the metabolite will often not require maximal levels of production, particularly when the bioassay is sensitive to small amounts of natural products. Thus initial submaximal production of compounds need not be a limitation to the success of the subject method.

Finally, as indicated above, the test sample can be derived from, for example, conditioned media or cell lystates. With regard to the latter, it is anticipated that in certain instances there may be heterologously expressed compounds which may not be properly exported from the host cell. For example, violacein is produced by recombinant *E. Coli*, yet the colonies turn purple without the plate surrounding the colony turning that color. This suggests that in order to detect the antibacterial activity of a violicein-like product, one would need to assay cell lysates. Their are a variety of techniques available in the art for lysing cells. A preferred approach is another aspect of the present invention, namely, the use of host cell-specific lysis agent. For instance phage (i.e. P1, λ, ϕ80) can be used to selectively lysis *E coli*. Addition of such phage to grown cultures of an *E. coli* host cells can maximize access to the heterolgous products of new biosynthetic pathways in the cell. Moreover, such agents would not interfere with the growth of a tester organism, e.g., a human cell, which may be co-cultured with the host cell library.

The following examples, though not intending to be limiting in any manner, provide further guidance.

A) Isolation and Structural Characterization of Active Compounds.

Once clones producing a compound with biological activity have been identified, the clones can be grown in large batches and active compounds purified from the scaled up process. The same cell-based and cell-free assays described above can also be used to monitor purification. Purification of the activities can be carried out using any of a number of techniques, and may be based on differential solubilities, thin layer chromatography, ion-exchange chromatography, and high-performance liquid chromatography, all of which are common practice in the art. Furthermore, structural determinations can be made on purified and semi-purified preparations of the activity.

B) High-Throughput Robotic Screening of BAC Clones for Production of Natural Products The high throughput processing and analysis of large genomic libraries by the subject method can be automated, e.g., using automated/robotic systems. The automation can include, for instance, such activities as: 1) arraying and storage of BAC libraries; 2) growth and separation of cells/conditioned culture media; and 3) testing conditioned media in biological and biochemical assays. These are outlined below for the exemplary embodiment of a BAC genomic DNA library. The detailed methodologies will vary from one embodiment to the next, but can be readily implemented by those skilled in the art.

Arraying and storage of BAC clones: Following ligation of the DNA into BAC vectors, the ligation mixture is transfected into a suitable host cell, and BAC-containing colonies are selected. If the number of clones recovered is small (e.g., less than 1000), then arraying into glycerol stocks can be accomplished manually. However, if libraries of more than 10,000 clones are obtained, then arraying is best accomplished using an automated colony picking robot.

Growth for expression of natural products and separation of culture: Clones can be inoculated for growth in deep-well 96-well plates, e.g., by using an automated pipetting station. Growth conditions can be established, e.g., using control strains. Following growth, culture media is isolated either by centrifugation and removal of supernatants or by filtration. Residual cells in the isolated culture media can be killed using chloroform vapors.

High throughput assays: The conditioned media can be tested for activity in high throughput biochemical or biological assays adapted for automated readouts. For instance, the method can employ established procedures for robotic antimicrobial testing. In general, such assays are performed in multi-well plates (96 or 384) or by placing small aliquots of conditioned media onto plates seeded with a bacterial or fungal lawn or the like. The goal is to develop an automated method that is sensitive and rapid. In addition to antimicrobial assays, as described above the culture supernatants can be tested in biochemical assays, such as competitive binding assays or enzyme activity assays, as well as whole cell assays, e.g., which detect changes in phenotype dependent on addition of conditioned media. To increase throughput, it may be desirable to test pools of culture supernatants in certain instances.

C) Screen the BAC Libraries for Activity Against Invertebrate Pests and Pathogens, Using Nematodes as the Model In one embodiment, the subject method can be used to create culture media which is tested for insecticidal activity. For instance, aliquots of BAC-expressed culture media can be added to culture of *C. elegans*, e.g., an easily culturable nematode. In other embodiments, the nematodes can be co-cultured with BAC-transformed bactera (the bacteria providing food for the nematodes, which are bacterial feeders). If the conditioned media or bacteria produce a nematicidal compound, then no growth will be seen. Clones that are active in this assay will be retested in a variety of insect bioassays to determine insecticidal activity.

VIII. Sequencing

Genomic clones identified in the subject assay can be isolated, and the sequence for the entire genomic fragment, or individual genes thereof, can be obtained by any of a number of sequencing methods known in the art. For instance, Sanger or Maxam and Gilbert sequencing can be performed. In other embodiments, the sequence can be obtained by techniques utilizing capillary gel electrophoresis or mass spectroscopy. See, for example, U.S. Pat. No. 5,003,059. Such techniques are preferred for automation of the sequencing step.

In certain embodiments, it will be desirable to fragment the genomic DNA insert, e.g., by restriction mapping, sequence the various inserts, and reassemble the full-length sequence. For very large inserts in BAC, PAC and P1 clones, it may be difficult to construct detailed restriction maps, e.g., with large number of restriction fragments leading to ambiguity of mapping data. However, the use of a recombinase to linearise and asymmetrically introduce a label at the unique recombinase recognition site of large clones. Subsequent partial digestion allows the direct ordering of restriction fragments. Efficient Cre-lox linearisation of BACs and applications of such techniques to physical mapping are decribed by, e.g., Mullins et al. (1997) *Nucleic Acids Res* 25:2539–40.

Merely for illustration, the following exemplary description of a preparation protocol will provide guidance for isolation of large clones for direct sequencing reactions. This protocol can be used to prepare clones such as BACs, PACs, cosmids or fosmids for direct sequencing reactions. Before starting the growth steps, it is important to find out what type of cloning vector was originally used—cosmid, fosmid, PAC or BAC, and what antibiotic resistance marker is carried by the vector. This will determine the culture volume to be prepared, as well as the antibiotic to be used, and its concentration. For instance, cosmids are multicopy vectors (e.g. many copies of the cosmid exist in each cell), so a 5–10 ml growth volume should be sufficient. On the other hand, fosmids, PACs and BACs are present one per cell ("single copy vectors"), and require a 12–15 ml growth volume to prepare sufficient DNA for sequencing reactions. Thus, the following protocol is based upon a 5 ml growth volume, where increased culture volumes will require that reagent volumes be scaled up accordingly.

1. Pellet cells from a 5 ml overnight growth by centrifugation for 5 minutes at 3500 rpm in the Jouan centrifuge, using the appropriate carrier. Discard the supernatant over a sink and invert the tubes onto clean paper toweling for 5 minutes to drain.
2. Add 400 $\mu$l of GET buffer plus RNase A (use 10 $\mu$l of 10 mg/ml RNase A [DNase free] per 1 ml of GET buffer stock) to each tube. Mix on the vortexer or by P1000 pipet (up/down pipetting) until a suspension without clumps of cells is obtained.
3. Using a P1000, transfer the resuspended cells to a clean 1.5 ml microcentrifuge tube for each sample.
4. Add 400 $\mu$l of freshly prepared lysis solution (2 ml of 5 N NaOH, 5 ml of 10% SDS and 43 ml of ddH2O) to each tube. Mix gently by inversion and place on ice for 5 minutes.
5. Add 400 $\mu$l of 3M KOAc, pH 4.8 to each sample. Invert several times to mix and place on ice for 5 minutes. A thick white precipitate should form once the solution is mixed.
6. Centrifuge for 5 minutes to pellet the chromosomal DNA and cell debris. While centrifuging, label two clean microcentrifuge tubes per sample. Place 600 $\mu$l of phenol:chloroform per tube.
7. Using a P1000, remove 600 $\mu$l aliquots of the resulting supernatant from each prep into the two phenol-containing tubes. Cap the tubes and vortex for 10–20 seconds. Spin for 5 minutes to separate phases. While centrifuging, label two clean microcentrifuge tubes per sample. Place 600 $\mu$l isopropanol per tube.
8. Using a P1000, remove the upper phase (~600 $\mu$l) to the isopropanol-containing tubes. Cap the tubes and invert several times to mix.
9. Centrifuge for 15 minutes to pellet the DNA. Discard the supernatant.
10. Wash each pellet with the addition of 1 ml of 70% ethanol. Spin 5 minutes and decant the wash. Dry briefly under vacuum.
11. Resuspend the DNA pellet in 20 $\mu$l* ddH2O. For large clones, checking the DNA on an agarose gel first requires digestion with a common restriction enzyme, such as Eco R1 or Hind III. Consult with library core on their choice for your particular clone, set up the digest, and electrophorese on a 1% agarose gel for 45–60 minutes to check the digestion. Proceed with sequencing if the digest appears on the gel as discrete fragments of reasonable intensity.

* Note: this is the only volume in the protocol that should not be scaled up. In other words, always resuspend the DNA pellet in 20 $\mu$l of water regardless of the starting volume of culture.

The following protocol can then be used either to sequence directly from CsCl banded cosmid clones (obtained from Library Core) or from alkaline lysis prepared cosmid, BAC, PAC or fosmid clones according to, for example, the above procedure for large clone DNA preparation.

Reaction Assembly:

| Per sample add the following in a fresh 0.2 ml tube: | |
|---|---|
| Taq FS Prism premix | 8 μl |
| Primer @ 3–10 uM | 1 μl |
| cosmid/BAC/PAC or fosmid DNA | μl (400 ng/rxn) ddH20 to 20 μl |
| Total | 20 μl |

Thermal Cycling: Cycle reactions as follows:
95° C. for 15 seconds
45° C. for 5 seconds
60° C. for 2 minutes
repeat for a total of 15 cycles
4° C. hold Precipitation: When samples have completed cycling add: 2.0 μl of 3M NaOAc, pH 5.2 100 μl of 100% EtOH. Then transfer the samples into a fresh 1.7 ml microcentrifuge tube. Spin reactions at 13,000 r.p.m. for 15 minutes. Wash 1× with 250 μl of 70% EtOH with a 5 minute spin. Decant EtOH, dry in speed vac and store at −2° C. Resuspend in 2 μl of dye and load onto a 377.

BAC End-Sequencing
1. For every 4 mls of culture, dissolve the BAC DNA pellet in 40 μl of water. for example: Usually each BAC is grown in 20 mls LB/CM total, then is dispensed into one Autogen tube (4 mls in each of the 5 tubes). After miniprep, add 40 μl of water to each tube (200 μl total for each BAC).
2. Vortex the Autogen tube and let sit for at least 0.5 hour. Then pool the 5 samples into one for each BAC.
3. check the BAC DNA for quality and quantity by digesting 5 μl of the DNA in a 20 μl reaction: 5.0 μl DNA
2.0 μl 10× Buffer 2 (NEB)
0.5 μl Hind III (NEB)
12.5 μl H$_2$O
Digest for 2–4 hours at 37° C.
4. Run the digest on a 0.8% agarose gel until the xylene cyanol line is at least 1 inch below the wells. There should be a strong band pattern for each BAC.
5. If DNA is OK for end-sequencing, then prepare 2 reactions for each BAC using T7 and SP6 primers (18 mers).
1 reaction: 22.0 μM DNA
16.0 μM reaction mix (ABI/PE #402122)
25 μM T7 or SP6
PCR conditions: 96° C. 4 min.
then 25 cycles of:
96° C. 10 sec.
50° C. 5 sec.
60° C. 4 min.
6. After PCR, purify samples in columns (Pharmacia #27-5340–03).
Column protocol:
1) vortex column;
2) break off tip at bottom;
3) place column in eppendorf tube and spin for 1 min. at 3000 rpm;
4) add all of reaction (40 μl) to top of gel column and place in a new tube;
5) spin again for 1 min. at 3000 rpm;
6) speedvac flow-through until all liquid has evaporated;
7) give dried reaction to sequencing facility.

IX. Exemplary Uses

There are a wide range of uses for the natural products which can be identified by the subject method. Secondary metabolites produced by microorganisms, such as fungi, reflect a wide variety of chemical structures affecting numerous biological activities in different classes of organisms, including both prokaryotes (bacteria) and eukaryotes (animals, plants, and insects). Antibiotics constitute the largest group of known bioactive secondary metabolites, acting on such diverse processes as cell wall synthesis, DNA replication, and protein synthesis. In addition to their use as antibiotics, secondary metabolites are being successfully developed and used in agriculture as pesticides, herbicides, and anti-parasitic compounds, and in treating non-infectious human diseases as inhibitors of enzyme To further illustrate, in animal therapies, the present method may be used to provide, e.g., angiogenesis inhibitors, insecticidal agents, antibacterial agents, antifungal agents, antiprotazoan agents, antiinflammatory drugs, antiparasitic agents, antitumor agents, cell cycle regulators, cytotoxic drugs, immune stimulants, immunosuppressants, ion channel blockers, fibrinolytic agents, free radical scavengers, prostaglandins and precursors, vasodilators, hypolipidemic agents, viral inhibitors (including reverse transcriptase and protease inhibitors), and modulators of microtubule dynamics, receptor-ligand interactions and enzyme activity (inhibitors or activators). the subject method can also provide biological activity molecules for use in agricultural applications, such as antibiotics, antifeedants, bactericides, enzymes with antibiosis activities (lysozymes, chitinases, glucanases, cellulases), fungicides, herbicides, pesticides (e.g., antihelminthics, insecticides, acaricides, anticoccidials, antitreponemals, and antitrichomonals), ion channel blockers and promoters, miticides, nematicides, pheromones, siderophores, viricides and the like. The subject method can also produce compounds which have applications in the the food industry, such as may be useful as enzymes, fatty acids, flavorings, gums, novel carbohydrates, peptides, pigments and dyes, sweeteners, and vitamins. Still other industrial applications include compounds and/or gene products useful in bioremediation (e.g., degradation of pesticides, toxic waste, oil, grease), as biotech enzymes (restriction enzymes, new reporter genes, antibiotic resistance markers), as industrial enzymes (amylases, proteases, lipases, phosphatases), or as new sources of polysaccharides (lubricants, thickeners). The ability of the polygenomic libraries of the subject method, e.g., through combinatorial biology based on microbial recombination, to create natural products having such activities can be assessed using standard methods in the art (see, e.g., Franco et al. (1991) *Crit. Rev. in Biotech.* 11:193–276, and references therein). The subject method, therefore, can further involve the use of, inter alia, biochemical assays, cell or tissue culture assays, and animal model systems. Several exemplary embodiments of these assays are described further below.

Antibiotic Activities

In one aspect, the method of the present invention can be used to discover products in the extracts of the engineered cells which display some antibiotic activity, e.g., antibacterial, antifungal and/or antiviral. Historically, discovery of antibiotics occurred through evaluation of fermentation broths for anti-bacterial or anti-fungal activity. For instance, many proteobacteria produce β-lactam antibiotics. This has been documented in *Chromobacterium, Pseudomonas, Agrobacterium, Serratia,* and *Erwinia* (de Lorenzo et al. (1984) *TIBS* 9: 266). Additionally, production of metabolites having antifungal activity, such as phenazines and phloroglucinols, have been documented in *Pseudomonas* (see, for example, Buysens et al. (1996) *Appl. Environ. Microbiol.* 62:865–871). Myxobacteria have emerged as major producers of novel biologically active compounds (Reichenbach et al., 1993, in *Third International Conference on the Biotechnology of Microbial Products: Novel Pharmacological and Agrobiological Activities. Developments in Industrial Microbiology Series* Volume 33. V. P. Gullo, J. C. Hunter-Cevera, R. Cooper, and R. K. Johnson, eds. Society for Industrial Microbiology). Therefore, extracts from the combinatorial gene systems of the present invention should be an excellent and abundant source of compounds (e.g., new metabolites) having antibiotic activities.

Anti-bacterial activities can be identified using a number of standard assays known in the art. For example, a culture of bacteria, such as a bacterial lawn, can be contacted with an extract from the host cell culture, e.g., filter paper discs doped with the extract, and the areas of lysis characterized. In other embodiments, the extracts are added to a liquid culture of a target organism, and the inhibition of bacterial cell growth can be determined, e.g., by turbidimetric readings. In addition to detecting general effects on bacterial growth and viability, the screening methods of the invention can involve assaying for effects on bacteria-specific structures, enzymes, or processes.

A large number of antifungal compounds have been identified using classic approaches, e.g., evaluating samples in primary tests directly against a range of filamentous fungi and yeasts, e.g., Candida albicans, grown in agar plates, or in some cases, directly against phytopathogenic infestations (Bastide et al. (1986) Mircen J. Appl. Microbiol. Biotechnol. 2:453; and Haruo, (1987) Gendai Kagaku Zokan 9:16). Such asssays can be readily adapted for use in a detection step of the subject method. Several examples of fungi-specific targets include chitin and glucan synthases (Selitrennikoff et al., (1983) Antimicrob. Agents Chemother. 23:757; Kirsch et al., (1986) J. Antibiot. 39:1620; and Denisot et al., (1990) 9th Int. Symp. Future Trends in Chemother., Geneva, March 26 to 28, page 47), and cutinases (Koller et al., (1990) J. Antibiot. 43:734; Umezawa et al. (1980) J. Antibiot. 33:1594).

To further illustrate, compounds which modulate sterol biosynthesis have valuable pharmacological properties. In particular, they can have a pronounced antifungal activity, e.g., such as ketoconazole and terbinafine. These compounds can accordingly be used as medicaments, especially for the control or prevention of topical or systemic infections which are caused by pathogenic fungi in mammals.

Ergosterol is the principal membrane sterol of fungi. It is structurally similar to its animal counterpart, cholesterol, except that ergosterol has a methyl group and two double bonds not present in cholesterol. In yeast, ergosterol affects membrane fluidity and permeability and plays an essential role in the yeast cell cycle. Yeast cells can take up cholesterol and decrease their requirement for ergosterol to very low levels, but cholesterol alone cannot completely substitute for ergosterol (Gaber et al. (1989) Mol. Cell. Biol. 9:3447–3456). Though the biosynthesis of ergosterol in fungi involves steps distinct from cholesterol biosynthesis in animals, sterol biosynthesis in different organisms share many common steps. Implicated in sterol biosynthesis is at least one cytochrome P450. The term "cytochrome P450" is a trivial name for a class of cytochromes that includes a number of heme proteins exhibiting a characteristic absorption maximum at 450 nm when combined with CO in the reduced state ('P' denotes pigment; hence, the name). These cytochromes occur in most animal tissues, plants and microorganisms and catalyze the monooxygenation of a vast variety of hydrophobic substances, including lipophilic endogenous compounds and xenobiotics, serving as oxygenating catalysts in the presence of one or more electron-transfer proteins or redox enzymes.

In certain embodiments, the test extracts are screened for sterol biosynthesis inhibitors of potential use as fungicides or antihypercholesterolemic agents identifies agents by the induction of lanosterol 14-?-demethylase, an enzyme in the biosynthetic pathway of ergosterol and cholesterol, in cultures containing the agents. Test samples which inhibit ergosterol biosynthesis in this system induce lanosterol 14-?-demethylase activity in the culture. In one screening test, test samples are incubated in a culture of a *Saccharomyces cerevisiae* strain sensitive to ergosterol biosynthesis and containing a gene fusion of a lanosterol 14-?-demethylase clone with a gene for bacterial β-galactosidase. After incubation of the culture, an increase in lancsterol 14-α-demethylase activity is determined indirectly by measuring β-galactosidase activity. The culture media contains a chromogenic substrate of β-galactosidase such as orthonitrophenyl-β-D-galactoside or 5-bromo-4-chloro-3-indoyl-β-D-galactoside, so that active samples are identified by the production of colored product. For comparison purposes, screening tests may employ a lanosterol 14-α-demethylase inhibitor such as dinaconazole as a positive control.

Anti-viral antibiotics can be identified by screening for inhibitors of virus-specific enzymes, such as retroviral reverse transcriptases. Other virus-specific processes, such as viral uncoating, viral receptor binding, and cell fusion (e.g., syncytium formation caused by HIV) can also be targeted in the screening methods of the invention.

The antiviral properties of the compounds may be determined in an assay which utilizes the unique properties of the virus. For instance, the influenza virus is a negative strand virus with a segmented genome. The synthesis of viral mRNA is accomplished by a virally-encoded transcription complex. Influenza virus is unique in that it requires capped and methylated palmers which are obtained from host cell RNA polymerase H transcripts to initiate mRNA synthesis. An in vitro influenza transcription assay was established to detect agents that may be present in natural product extracts that are capable of inhibiting the transcription apparatus of the influenza virus.

U.S. Pat. No. 5,624,928 describes an exemplary assay for detecting inhibitors of the transcription apparatus of the influenza virus which are required to initiate viral mRNA (messenger RNA) synthesis. Briefly, to each well of a 96-well microtiter plate is added a stock mix of the virus, the test sample, labeled nucleotides, and water. Ten microliters of primer (alfalfa mosaic virus (ALMV) RNA at 0.015 mu g/ml) is also added to the wells. The plates are gently mixed on a shaker for 30 seconds and then incubated for 60 minutes in a 31 o C. water bath.

At the end of this period, the plates are removed from the water bath, placed on a bed of ice and the reaction stopped with (i) sterile saturated sodium pyrophosphate solution containing 0.5 mg/ml RNase-free tRNA and (ii) ice-cold 40% TCA, and the plates allowed to stand on ice for 15 minutes. The samples are then collected, using a cell harvester, washed twice with 5% TCA, then twice with 95% ethanol and then transferred to sealing bags. The incorporation of the labeled nucleotides into a reverse transcript of the ALMV RNA is detected.

Anti-Tumor Activities

To identify anti-tumor activities, cultured tumor cell lines or cultured tumors can be contacted with culture extracts, or by co-culturing with the host cells, and effects on cell growth and viability monitored. Another approach involves screening for products from the host cells which induce differentiation of tumor cells, e.g., which causes these cells to lose their tumorigenicity (Franco et al., (1991) *Crit. Rev. in Biotech.* 11:193–276). An in vitro disease oriented screening program can utilize a large panel of human tumor cell lines grown initially in vitro and assessed for cytotoxicity by the MTT assay (Carmichael et al. (1987) *Cancer Res* 47:936–42) and subsequently the sulforhodamine B protein assay (Skehan et al. (1991) *Eur J Cancer* 27:1162–8). The aim of this screen is to select test extracts exhibiting selective activity against different histological tumor types.

Enzymes can also be used as targets for identifying anti-tumor activities. Enzymes that have been successfully employed as targets in the search for anti-tumor agents include protein tyrosine kinases, which are components of signal transduction pathways regulated by a number of oncogenes, phosphatidylinositol kinase, spermidine synthase, and topoisomerases. As the differences between tumor and non-tumor cells become more apparent, tumor cell-specific targets can be used in the screens in order to identify activities that are not toxic to the patient.

Extracts that exhibit anti-tumor activities in biochemical and cell culture assays can be tested further in appropriate animal model systems.

Immunosuppressive Activities

Immunosuppressive activities can be identified using a number of standard methods in the art, including the mixed lymphocyte reaction, which measures lymphocyte proliferation (Goto et al., (1982) *J. Antibiot.* 35:1286), and screens for macrophage activation (Tanida et al. (1989) *J. Antibiot.* 42:1619). Inhibitors of T cell activation can be identified by growing cultured T cells in the presence of the candidate extract, crosslinking with activating agents, such as antibodies to CD3 and CD4 surface molecules and a secondary antibody, which normally activate T cells, and determining the level of T cell activation. T cell activation can be quantified by, e.g., a bioassay in which IL-2 production is measured by applying the T cell culture supernatant to CTLL-20 cells, which require IL-2 to live (Sleckman et al., (1987) *Nature* 328:351).

The cellular immune response involves a very complex set of interactions between antigens, T cells, B cells, macrophages, and numerous factors, such as cytokines, which are released by the cells during the course of the interactions. In one embodiment, the test extracts can be tested for effect on T cell activation. While specificity of the T cell response is determined by antigen-specific binding to the T cell antigen receptor (TCR), binding to at least one secondary receptor is also necessary for activation. One such secondary receptor is CD28 which, upon stimulation, induces the activity of nuclear proteins which can increase the production of interleukin-2 and possibly other cytokines by binding to an enhancer region associated with the cytokine genes. Immunosuppressive drugs which act by suppression of the CD28 pathway may have a number of advantages over drugs which act through other mechanisms. Thus, according to the present invention, screening assays for immunosuppressive compositions can comprise exposing cultured T cells to test extract, where the T cells produce an observable signal as a result of normal CD28 stimulation. The T cells are cultured under conditions which will, in the absence of effective CD28 stimulation, produce the observable signal, generally requiring the presence of substances which result in stimulation of both CD28 and the T cell receptor (TCR). The assay can thus identify test extracts that at least partially suppress the stimulation of CD28, thus resulting in a decrease in the observable signal.

T cells used in the screening assays of the present invention can be obtained from T cell lines which have been modified to stably incorporate a CD28 enhancer region in reading frame with a reporter gene so that exposure of the cells to conditions selected to induce the CD28 receptor will result in expression of the reporter gene. The T cell lines may be derived by modifying previously established human or mouse T cell lines and hybridomas, where the starting cell lines and hybridomas are capable of expressing certain cytokine gene(s), as discussed below.

A variety of cell lines suitable for modification according to the present invention are available from public depositories, such as the American Type Culture Collection (A.T.C.C.), Rockville, Maryland. Exemplary cell lines include Jurkat or HUT-28, human leukemic T cell lines; EL-4, a mouse T cell line; BW5147, a mouse cell line; 2B4, a mouse hybridoma cell line; and human or mouse T cell clones.

The CD28 enhancer region may be derived from the 5' flanking region of a cytokine gene, where the cytokine gene selected should be one which is normally expressed in the cell line being modified. The enhancer region will include at least that portion of the 5' flanking region which is bound by the CD28 nuclear protein which is produced as a result of stimulation of the CD28 receptor, as described below, Suitable enhancer regions may be obtained from such genes as the IL-2 gene, the GM-CSF gene, the IL-3 gene, the G-CSF gene, or the γ-IFN gene.

Extracts found to possess immunosuppressive activity in the cell culture assays can be further tested in animal model systems. An extract containing a candidate compound, or a purified or semi-purified fraction thereof, is administered to an immunocompetent animal, for example, a mouse which has a non-MHC matched skin graft, and the effect of the compound on, e.g., T cell or macrophage activation is determined by monitoring the immune response of the mouse.

As mentioned above, preferable screening assays are designed to identify biological activities directed specifically against the target cell, e.g., an infectious pathogen or a tumor cell, and not cells of the host organism, in order to decrease the likelihood of toxicity problems. Especially in cases where the potential therapeutic biological activity is directed against a process or structure which may be similar in the target cell and the host, it is critical to determine the relationship between the effectiveness and the toxicity of the treatment. This can be determined by standard methods using both cell culture assays and animal model systems (*The Pharmacological Basis of Therapeutics*, eds. Goodman and Gilman, MacMillan Publishing, New York, 1980, pp. 28–39, and 1602–1614).

Lipid Biosynthesis

The subject method can also be used to identify genes involved in lipid biosynthesis, as well as novel lipids produced by the products of these genes. To illustrate, surface-exposed unusual lipids containing phthiocerol and phenol-phthiocerol are found only in the cell wall of slow-growing pathogenic mycobacteria and are thought to play important roles in host-pathogen interaction. The enzymology and molecular genetics of biosynthesis of phthiocerol and phenolphthiocerol are unknown; though it has been postulated that a set of multifunctional enzymes are involved in their synthesis, and that these genes are clustered on the bacterial genome. Azad et al. (1997) *J Biol Chem* 272: 16741–5.

Polysacchride Biosynthesis

Yet another class of molecules which can be produced by the chimeric host cells are include novel polysaccharides. For instance, alginate is an unbranched polysaccharide composed of the two sugar residues beta-D-mannuronic acid (M) and alpha-L-guluronic acid (G). The M/G ratio and sequence distribution in alginates vary and are of both biological and commercial significance. As with the PKS and lipid biosynthetic pathways, the genes involved in alignate biosynthesis are also believed to be localized in clusters, and hence are likely to be isolatable in large part in single genomic clones.

Modulators of Extracellular Factors

In one embodiment, the test extracts can be assayed for their ability to alter the bioactivity of an extracellular protein, lipid, carbohydrate or the like. For instance, the assay can be disposed to identify inhibitors of blood coagulation factors, thrombolytic factors, or enzymes aberrantly upregulated in diseases states, such as superoxide dismutase or the like.

Ligands for Cell Surface Receptors.

In another embodiment, the subject method can be use to identify ligands for cell surface receptor protein or ion channel, e.g., proteins which interact with an extracellular molecule (i.e. hormone, growth factor, peptide, ion) to modulate a signal in the cell. Exemplary receptors include: a receptor tyrosine kinase, e.g., an EPH receptor; an ion channel; a cytokine receptor; an multisubunit immune recognition receptor; a chemokine receptor; a growth factor receptor; or a G-protein coupled receptor, such as a chemoattracttractant peptide receptor, a neuropeptide receptor, a light receptor, a neurotransmitter receptor, or a polypeptide hormone receptor. In addition, the subject assay is amenable to identifying ligands for an orphan receptor, i.e., a receptor with no known ligand, regardless of the class of receptors to which it belongs.

In certain embodiments, the receptor is a G protein coupled receptors, such as α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 ACHR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor receptor, antidiuretic hormone receptor, glucagon receptor, and adrenocorticotropic hormone II receptor.

In other embodiments, the receptor is a receptor tyrosine kinase, e.g., an EPH receptor such as eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors.

The modulation of cell surface proteins can also include effecting the bioactivity of the adherin proteins, e.g., cadherins, integrins and the like.

In certain embodiments the subject assays measure the production of second messengers to determine changes in ligand engagement by the receptor. A "second messenger" is defined as an intermediate compound whose concentration, either intercellularly or within the surrounding cell membrane, is raised or lowered as a consequence of the activity of an effector protein. Some examples of second messengers include cyclic adenosine monophosphate (cAMP), phosphotidyl inositols (PI), such as inositol triphosphate (IP3), diacylglycerol (DAG), calcium (Ca++) and arachidonic acid derivatives. In preferred embodiments, changes in GTP hydrolysis, calcium mobilization, or phospholipid hydrolysis can be measured. In other embodiments, the test cells contain a reporter gene which is sensitive to signalling by the target receptor.

Modulators of Intracellular Signalling.

Still another class of molecules which can be identified in the assay of the present invention are those which modulate intracellular signalling, e.g., by inhibiting or potentiating protein-protein (intermolecular or intramolecular interactions), protein-DNA, protein-lipid or protein-2nd messanger interactions, inhibiting or potentiating intracellular enzymes, or inhibiting or potentiating ion channel passivity, and the like. As described above, the test extract can be sampled with purified or semi-purified components, lysates, whole cells or any other convenient way of contacting the products of the recombinant host cell with the intended target in a manner which permits generation of a detectable signal. That signal may be, for instance, a change in the a cell's phenotype, rate of proliferation or survival, transcription of a reporter gene, changes in $2_{nd}$ messanger levels, a change in an enzymes activity towards a detectable substrate (or one which produces a detectable product), a change in the amount or characteristics of protein complexes or the localization of a protein, e.g., within various cellular compartments. To further illustrate, the detection step of the instant assays can be derived to identify products of the recombinant host cell that, for illustration, modulate a protein kinase (e.g., serine/threonine kinase, tyrosine kinase), a protein phosphatase (e.g., serine/theronine phosphatase, tyrosine phosphatase), interactions mediated by SH2 domains (e.g., with phosphotyrosine residues), interactions mediated by SH3 domains, interactions mediated by leucine zipper domains, phosphatidyl inositol kinases, adenyl cyclases, interactions involving G proteins (e.g., with a G protein coupled receptor, between the α subunit with β/γ dimer, or downstream signal transduction proteins), phospholipases, phosphodiesterases, interactions between DNA binding proteins and DNA, and ion flux through ion channels. The interactions can occur between components of the same cell compartment, as between two intracellular proteins, or different compartments, such as between a cell surface receptor and an intracellular signal transduction protein.

Selective Natural Products

In one embodiment, the assay can be used to identify novel polyketides. Polyketides are naturally-occurring compounds, most often produced by microorganisms such as fungi and the filamentous bacteria (the actinomycetes). The route by which these compounds are formed is one of the most widespread in nature. It is responsible for a vast array of natural products with structures varying from simple aromatic compounds like 6-methylsalicylic acid (6-MSA) to the gigantic polycyclic ether maitotoxin, whose molecular weight of 3422Da makes it the largest known secondary metabolite. Apart from microorganisms, polyketides are also isolated from a wide range of marine organisms (for example, brevitoxin) and higher plants (flavonoids). Many other metabolites contain polyketide-derived moieties as part of a larger structure from another biosynthetic origin, for example, the unusual amino acids, such as 4-[2-butenyl]-4-methyl-L-threonine (Bmt) found in cyclosporin, and algal peptide toxins and meroterpenoids such as tetrahydrocannabinol.

In addition to their wide occurrence and structural diversity, polyketides display a huge range of biological activities. These include antibiotics (for example tetracyclines and erythromycin), anti-cancer agents (daunomycin and dynemycin A), antifungals (griseofulvin and strobilurins), antiparasitics (avermectin and monensin), immunosuppressive agents (FK506 and rapamycin), and cholesterol-lowering agents (lovastatin and squalestatins). Thus they have long been of interest to scientists from many disciplines, including natural product chemists, microbiologists and pharmacologists. Many of the challenging synthetic targets currently being worked on by organic chemists are polyketides.

Despite their enormous structural variety, all of the polyketides are related by their common biosynthetic origins (O'Hagan et al. (1995) *Nat. Prod. Rep.*, 12:1). They are derived from highly functionalised carbon chains whose assemblies are controlled by multifunctional enzyme complexes called polyketide synthases. Like the closely related fatty acid synthases, polyketide synthases catalyse a repetitious sequence of decarboxylative condensation reactions between simple acyl thioesters and malonate. Each condensation is followed by a cycle of modifying reactions: ketoreduction, dehydration and enoyl reduction.

Several individual enzymes are needed during the assembly of a fatty acid or a polyketide. These enzymes—ketosynthase, ketoreductase, dehydratase, enoyl reductase—carry out the main chemical transformations in the assembly sequence. In addition, an acyl carrier protein, acyl and malonyl transferases and thioesterases are needed to load substrates and remove products. For aromatic polyketides, the participation of one or more cyclases is also essential. Genetic analysis of fungal and bacterial polyketide synthases has revealed that they come in a number of distinct forms, and the current state of knowledge of these will be summarised in turn.

In bacterial systems, the polyketide synthases responsible for the biosynthesis of aromatic polyketide antibiotics are analogous to bacterial and plant type II fatty acid synthases. Here the synthase is made up of a functioning complex of essentially monofunctional proteins. In both the fungal type I and bacterial type II systems, it is important to emphasise that it is the same enzymes that are used repetitively in each cycle of chain elongation and modification. All of the genes necessary for the biosynthesis of the polyketide antibiotic actinorhodin in *Streptomyces coelicolor* were found together, 'clustered' on the same stretch of genomic DNA. This enables, by the subject method, all the biosynthetic genes to be readily isolated on a single genomic clone. From this and subsequent work, it has become clear that assembly and cyclisation of the intermediates in the biosynthesis of aromatic polyketides in Streptomycetes usually requires up to six individual gene sequences (referred to as open reading frames or ORFs) from the respective polyketide gene clusters. The remaining genes in the clusters are involved in the initiation and control of polyketide synthesis and the post assembly reactions which further elaborate the initial polyketide products to give the final observed structures.

Thus, DNA fragments containing the whole or part of the gene cluster can be introduced into a host cell, such as a Streptomycetes. In preferred embodiments, all or a portion of the corresponding gene cluster in the host cell can be inactivated/deleted. In the case where a chimeric pathway is generated in the host cell, a "hybrid antibiotic" can be produced, e.g., by the concerted genes from different, albeit related, biosynthetic pathways. Such compounds can be detected in, for example, by the assays described above for identifying antibiotic agents, e.g., by biological, biochemical or chemical means.

Another class of small molecule natural products which can be obtained by the subject method are the macrocyclic lactones. This group of compounds shares the presence of a large lactone ring with various ring substituents. They can be further classified into subgroups, depending on the ring size and other characteristics. The macrolides, for example, contain 12-, 14-, 16-, or 17-membered lactone rings glycosidically linked to one or more aminosugars and/or deoxysugars. They are inhibitors of protein synthesis, and are particularly effective against gram-positive bacteria. Erythromycin A, a well-studied macrolide produced by *Saccharopolyspora erythraea*, consists of a 14-membered lactone ring linked to two deoxy sugars. Many of the biosynthetic genes have been cloned from *S. erythraea*, all of which have been located within a 60 kb segment of that organisms genome; thus there is a reasonable prospect for isolating corresponding gene clusters.

Still another class of molecules which can be developed by the subject method are derivatives of quinones. Quinones are aromatic compounds with two carbonyl groups on a fully unsaturated ring. The compounds can be broadly classified into subgroups according to the number of aromatic rings present, i.e., benzoquinones, napthoquinones, etc. A well studied group is the tetracyclines, which contain a napthacene ring with different substituents. Tetracyclines are protein synthesis inhibitors and are effective against both gram-positive and gram-negative bacteria, as well as *rickettsias, mycoplasma,* and *spirochetes*. The aromatic rings in the tetracyclines are derived from polyketide molecules. Genes involved in the biosynthesis of oxytetracycline (produced by *Streptomyces rimosus*) have been cloned and expressed in *Streptomyces lividans* (Binnie et al. (1989) *J. Bacteriol.* 171:887–895). The PKS genes share homology with those for actinorhodin and therefore encode type II (monofunctional) PKS proteins (Hopewood et al. (1990) *Ann. Rev. Genet.* 24:37–66).

Derivatives of several other types of small molecule products are also likely to be identified by the subject method. One of these is the antibiotic 2-hexyl-5-propylresorcinol which is produced by certain strains of *Pseudomonas*. It was first isolated from the *Pseudomonas* strain B-9004 (Kanda et al. (1975) *J. Antibiot.* 28:935–942) and is a dialkyl-substituted derivative of 1,3-dihydroxybenzene. It has been shown to have antipathogenic activity against Gram-positive bacteria (in particular *Clavibacter* sp.), mycobacteria, and fungi. Another class are the methoxyacrylates, such as strobilurin B. Strobilurin B is produced by *Basidiomycetes* and has a broad spectrum of fungicidal activity (Anke et al. (1977) *Journal of Antibiotics* (Tokyo) 30:806–810). In particular, strobilurin B is produced by the fungus *Bolinia lutea*. Strobilurin B appears to have antifungal activity as a result of its ability to inhibit cytochrome-b dependent electron transport thereby inhibiting respiration (Becker et al. (1981) *FEBS Letters* 132:329–333.

Bioremediation

In yet another embodiment, the subject method can be used to isolate a gene, or set of genes, which produce enzymes useful in bioremediation processes, e.g., degradation of pesticides, toxic waste, oil, grease. In one aspect, the genomic DNA can be cloned from microorganisms originally present in a polluted region. In this case, the degrading ability of the microorganisms which have naturally grown by utilizing the pollutants as an energy source is extended, and the extended degrading activity is enhanced. In any event, the detection step of the assay can be generated with a purfied form of the hazardous (otherwise undesirable) material, with a whole environmental sample, or with some semi-purified fraction therebetween. Utilizing techniques well-known in the art, the ability of the gene or gene products to sequester or transform the hazardous material is detected for the test extract.

Nematicidal Agents

In another aspect, the subject methods are useful for the identification of genes, or biosynthetic products, which can be used to control pests and, particularly, plant pests. Specifically, the subject method can be used to identify new toxins useful for the control of nematodes. Certain gene isolates and toxins of the subject invention can also be used to control coleopteran pests, including corn rootworm.

Control of nematodes, or coleopterans, using such toxins, or if appropriate, the cloned genes, can be accomplished by a variety of methods known to those skilled in the art. These methods include, for example, the application of toxin to the pests (or their location), the application of recombinant microbes to the pests (or their locations), or, if appropriate, the transformation of plants with genes which encode the pesticidal toxins Exemplary assays formats for detecting nematicidal agents include:

a. The Split-pot test: the test detects an anti-nematode agents having a repellent or antifeedant effect on the nematodes and/or a nematicidal effect. A 'split-pot', i.e. a pot divided into two sections by a fine mesh material (see Alphey et al (1988) *Revue Nematol.* 11:399–404), can be used. Each side is filled with soil. Test extracts are added to the soil on the side in which a seedling (Petunia) has been planted. To the other side a population of nematodes, e.g., adult Xiphinema diversicaudatum, are added. After a certain period of time, the two halves of the pot are separated and the nematodes extracted from the soil in each half. Root galls are recorded on plants from the treated sides (antifeedant action). The numbers of live and dead nematodes from each half are also counted (nematotoxic effect).

b. Mini-pot test: This test identifies the nematicidal effect of present in a test extract in soil and its effect on nematode feeding behaviour. Briefly, seedlings (Petunia) are planted in soil. The test extracts, along with a population of nematodes, is added to the soil. Some time later, the nematodes are extracted and the number of galls induced by nematode feeding on the roots are determined.

Identification of Compounds Responsible for the Biological Activities

The biological activity can be further characterized by purifying the compound(s) responsible for the activity using standard methods, such as liquid-liquid, liquid-solid, or affinity chromatography with normal phase, reverse-phase, ion-exchange, and gel filtration techniques being implemented as needed (Box, (1991) in *Discovery and Isolation of Microbial Products*, Verall, M. S., Ed., Ellis Horwood, Chichester, 1985; Franco et al. (1991) *Crit. Rev. in Biotech.* 11:193–276). The purification can be monitored by co-fractionation of the biological activity, using any of the screening assays described above. Once purified, the structure of the compound can be determined using standard methods, including nuclear magnetic resonance, mass spectroscopy, and X-ray crystallography.

X. Exemplfication

The invention now being generally described, it will be more readily understood by reference to the following examples which are included merely for purposes of illustration of certain aspects and embodiments of the present invention, and are not intended to limit the invention.

EXAMPLE 1

BAC Library of *Bacillus cereus* DNA

We have constructed a library in pBeloBAC11 from *B. cereus* strain UW85. Briefly, the UW85 cells were embedded in agarose plugs, and cellular components (other than DNA) were removed by treatment of the plugs with lysozyme, proteinase K and detergent. The DNA was digested in situ, and size fractionated on a preparative agarose gel in order to isolate size fragments of interest. The average insert size was 76 Kb and some of the clones contain inserts as large as 170 Kb. The genomic DNA was ligated into a BAC vector and used to transform *E. coli* DH10B, where the inserts we observed to be stable. We screened the library for 10 phenotypes that are easily tested in culture and found a total of 9 clones that were positive for 5 of the phenotypes, which were: esculin hydrolysis, ampicillin resistance, lysis of red blood cells, clearing of lecithin, and resistance to zwittermicin A. Since *B. cereus* is genetically quite different from *E. coli* based on codon usage and base content (*B. cereus* is 35% GC whereas *E. coli* is 50% GC), it is quite encouraging that we found such a high frequency of gene expression in the *B. cereus* BAC library in *E. coli.*

These experiments demonstrate that half of the traits tested were expressed in an *E. coli* BAC clone bank of DNA from *B. cereus*, which is an AT-rich, Gram-positive bacterium, thereby supporting the prediction that genes from many soil bacteria will be expressed in the BAC library. Second, we have shown that soil DNA is readily cloned in the BAC vector.

EXAMPLE 2

Construction of Library of Soil DNA

We isolated soil DNA by use of the agarose plug system above, and cloned genomic DNA fragments into pBelo-BAC11. Briefly, 5 g of soil was mixed with 13.5 ml extraction buffer (100 mM Tris-Cl, pH 8; 100 mM EDTA; 100 mM sodium phosphate, pH 8; 1.5M NaCl; 1% CTAB). To that suspension was added 1.5 mL of 20% SDS. The mixture was freeze-thawed two times for 10 minutes, e.g., in a dry ice-ethanol bath, followed by 10 minutes at 60° C., and then incubated for 2 hours at 60° C. The preparation was then centrifuged at 6000×g for 10 minutes at 27° C. The preparation was transferred to a new tube and mixed with equal volumes of $CHCl_3$ and isoamyl alcohol. The aqueous phase was recovered by centrifugation and precipitated with 0.6 volumes of isopropanol at 27° C. for 1 hour. The DNA pellet was recovered by centrifugation at 16,000×g for 20 minutes at 27° C., washed with 70% ethanol, and resuspended in 500 µl buffer.

DNA was further purified by preparative gel electrophoresis, producing a size range of 25–125 kb. The DNA was digested with HindIII and ligated to the pBeloBAC11 vector and transfected into E coli. By this method, we have obtained a total of more than 3,700 clones and we have characterized 85 of them in detail. Thusfar, all of the clones screened contain inserts, and the inserts have an average size of 28 Kb and a range of 13 to 60 Kb. Considering that we used methods that shear DNA during isolation, the large size of these inserts suggests that the target of 100 Kb inserts is attainable when we use gentler methods. In an initial screen, we found 8 clones that degrade esculin, an ability that the host E. coli strain does not have.

EXAMPLE 3

Detection of Clone Possessing Antibacterial Actvity in Library of Soil DNA

As described above, the subject method can be used for the discovery of compounds with antibiotic activity, e.g., against *Staphylococcus* and *Enterococcus*, since multidrug resistant strains of various bacteria are become more common and are a significant threat to human health. Briefly, 78 plates, each containing 40 clones, were replicated to LB plates with 6.25 µg/ml chloramphenicol. The plates were incubated for 48 hours at 37° C. A soft agar overlay was applied to the plates. This contained 1.3 ml LB medium, 0.2 ml of an overnight culture of *S aureus*, and 1.5 ml of 0.8% agar. The plates were examined after 24 hours of incubation at 37° C.

One of the clones showed a clear zone around it, indicating that a substance was produced which inhibited growth of the *S aureus* cells in the overlay. The clone was colony purifed, and plasmid DNA was isolated from a culture. The plasmid was electroporated into the same *E coli* strain background as had been used in the initial screen, and the resulting transformants were retested to confirm that the *S aureus* inhibitory activity was in fact due to a plasmid-encoded activity.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for detecting a compound produced by a biosynthetic pathway, comprising:
   i) isolating genomic DNA from a source containing uncultivated microorganisms, without an intervening step of culturing cells from the source, by mixing the source with an extraction buffer and lysing the microorganisms to obtain isolated genomic DNA; and then
   ii) inserting the isolated genomic DNA of step (i) into a replicable vector to obtain clones of the replicable vector comprising the isolated genomic DNA; and then
   iii) introducing the clones of step (ii) into host cells to obtain a library of host cells, wherein the isolated genomic DNA in at least some of the clones is at least 50 kb; and then
   iv) culturing the host cells of step (iii) under conditions wherein an open reading frame sequence of the isolated genomic DNA is expressed by the host cells; and then
   v) detecting a compound produced by the host cells as a result of expression of the open reading frame sequence of step (iv).

2. The method of claim 1, wherein step (v) comprises detecting a non-polymeric compound.

3. The method of claim 1, wherein step (v) comprises detecting a non-proteinaceous compound.

4. The method of claim 1, wherein step (v) comprises detecting a compound having a molecular weight less than 7500 amu.

5. The method of claim 1, wherein step (v) comprises detecting a compound that is a direct product of endogenous precursors for the biosynthetic pathway.

6. The method of claim 1, wherein in step (iii) the isolated genomic DNA in the clones has an average length of at least 75 kb.

7. The method of claim 6, wherein in step (iii) the isolated genomic DNA in the clones has an average length of at least 100 kb.

8. The method of claim 1, wherein the source of microorganisms in step (i) includes prokaryotes.

9. The method of claim 8, wherein the source of microorganisms in step (i) includes prokaryotes of the *Archaea* Domain.

10. The method of claim 9, wherein the source of microorganisms in step (i) includes *Archaea* cells selected from the group consisting of *Crenarachaeota, Euryarachaeota, Karachaeota*, and combinations thereof.

11. The method of claim 1, wherein step (i) comprises isolating genomic DNA from a source selected from the group consisting of soil samples, insect intestines, plant rhizospheres, microbial mats, sulfur pools samples, or marine samples.

12. The method of claim 1, wherein the source of microorganisms in step (i) includes prokaryotes having low G/G content genomes.

13. The method of claim 1, wherein the source of uncultivated microorganisms in step (i) includes anaerobes.

14. The method of claim 1, wherein in step (iii) the library of host cells comprises a variegated population of vectors containing different isolated genomic DNA sequences.

15. The method of claim 14, wherein step (i) comprises isolating genomic DNA having an average length of at least 50 kilobases.

16. The method of claim 14, wherein in step (iii) the library of host cells comprises a variegated population of vectors including isolated genomic DNA from at least 10 different microorganism species.

17. The method of claim 1, wherein step (iii) comprises introducing the clones of step (ii) into host cells selected from the group consisting of *Acetobacter, Actinomyces, Aerobacter, Agrobacterium, Azotobacter, Bacillus, Bacteroides, Bordetella, Brucella, Chlamydia, Clostridium, Corynebacterium, Erysipelothrix, Escherichia, Francisella, Fusobacterium, Haemophilus, Klebsiella, Lactobacillus, Listeria, Mycobacterium, Myxococcus, Neisseria, Nocardia, Pasteurella, Proteus, Pseudomonas, Rhizobium, Rickettsia, Salmonella, Serratia, Shigella, Spirilla, Spirillum, Staphylococcus, Streptococcus, Streptomyces, Trepanema, Vibrio,* and *Yersinia*.

18. The method of claim 17, wherein step (iii) comprises introducing the clones of step (ii) into host cells selected from the group consisting of *Escherichia* and *Streptomyces*.

19. The method of claim 18, wherein step (iii) comprises introducing the clones of step (ii) into an *Escherichia coli* host cell.

20. The method of claim 1, wherein step (ii) comprises inserting the isolated genomic DNA into a low-copy number vector.

21. The method of claim 20, wherein step (ii) comprises inserting the isolated genomic DNA into a single-copy number vector.

22. The method of claim 20, wherein step (ii) comprises inserting the isolated genomic DNA into a BAC or PAC vector.

23. The method of claim 1, wherein step (v) comprises detecting the compound produced by the host cells as a result of expression of the open reading frame sequence of step (iv) by an ability of the host cell to induce a biological or biochemical response from a test cell.

24. The method of claim 23, wherein the biological or biochemical response induced in the test cell comprises: a phenotypic change, a change in gene transcriptional rates, a change in phosphorylation states, a change in 2nd messenger formation, cell quiescence, or cell death.

25. The method of claim 1, wherein step (v) comprises detecting the compound produced by the host cells as a result of expression of the open reading frame sequence of step (iv) by spectrometric detection.

26. The method of claim 1, wherein step (v) comprises detecting the compound produced by the host cells as a result of expression of the open reading frame sequence of step (iv) by chromatographic detection.

27. The method of claim 1, wherein step (v) comprises detecting the compound produced by the host cells as a result of expression of the open reading frame sequence of step (iv) using a cell-free assay.

28. The method of claim 1, wherein step (v) comprises detecting the compound produced by the host cells as a result of expression of the open reading frame sequence of step (iv) by inducing a biological or biochemical response from the host cell.

29. A method for detecting a product of a biosynthetic pathway, comprising:
   i) directly cloning into a replicable vector-genomic DNA isolated from a complex microbial sample without an intervening step of culturing cells from the sample, and size-fractionated prior to any enzymatic manipulation of the DNA to facilitate its insertion into the replicable vector, wherein at least some of the genomic DNA cloned into the vector is at least 50 kb long; and then
   ii) transforming the replicable vector of step (i) into host cells to obtain a library of host cells; and then
   iii) expressing open reading frame sequence(s) of the genomic DNA contained in the library of host cells of step (ii); and then
   iv) detecting a compound which is the product of a biosynthetic pathway that is dependent on expression of at least one of the opening reading frames of step (iii).

30. The method of claim 1, wherein step (i) comprises lysing the microorganisms and isolating the genomic DNA from the source by further treating the source with a protease and a detergent to yield a mixture, centrifuging the mixture to yield a supernatant, extracting the supernatant with chloroform in the absence of phenol to yield a chloroform fraction containing the genomic DNA, and precipitating the DNA by adding isopropanol to the chloroform fraction.

31. The method of claim 30, wherein step (i) further comprises size-fractionating the isolated genomic DNA prior to enzymatic manipulation of the DNA for insertion into the replicable vector of step (ii).

32. The method of claim 31, wherein step (i) comprises size-fractionating the isolated genomic DNA via electrophoresis.

* * * * *